(12) United States Patent
Furukawa et al.

(10) Patent No.: US 11,044,911 B2
(45) Date of Patent: Jun. 29, 2021

(54) PHENOXYUREA COMPOUND AND PEST CONTROL AGENT

(71) Applicant: Nippon Soda Co., Ltd., Tokyo (JP)

(72) Inventors: Hironori Furukawa, Kanagawa (JP); Takao Iwasa, Kanagawa (JP); Tomohiro Amano, Kanagawa (JP); Yasuyuki Shiinoki, Kanagawa (JP); Hiroko Moroe, Kanagawa (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 17/045,418

(22) PCT Filed: Apr. 3, 2019

(86) PCT No.: PCT/JP2019/014798
§ 371 (c)(1),
(2) Date: Oct. 5, 2020

(87) PCT Pub. No.: WO2019/198592
PCT Pub. Date: Oct. 17, 2019

(65) Prior Publication Data
US 2021/0051960 A1    Feb. 25, 2021

(30) Foreign Application Priority Data
Apr. 9, 2018    (JP) .............................. JP2018-074961

(51) Int. Cl.
*A01N 47/28* (2006.01)
*C07C 275/64* (2006.01)

(52) U.S. Cl.
CPC ............ *A01N 47/28* (2013.01); *C07C 275/64* (2013.01)

(58) Field of Classification Search
CPC .............................. A01N 47/28; C07C 275/64
See application file for complete search history.

(56) References Cited

U.S. PATENT DOCUMENTS

| | | | | |
|---|---|---|---|---|
| 9,029,601 | B2* | 5/2015 | Furukawa | A61K 31/47 564/47 |
| 9,334,259 | B2* | 5/2016 | Furukawa | A01N 41/06 |
| 9,580,384 | B2* | 2/2017 | Furukawa | A61K 31/415 |
| 2013/0231479 | A1 | 9/2013 | Furukawa et al. | |
| 2015/0099883 | A1 | 4/2015 | Furukawa et al. | |
| 2017/0035711 | A1 | 2/2017 | Iwasa | |

FOREIGN PATENT DOCUMENTS

| | | |
|---|---|---|
| CN | 105859590 A | 8/2016 |
| CN | 106232112 A | 12/2016 |
| JP | 61-126065 A | 6/1986 |
| JP | 62-120353 A | 6/1987 |
| JP | 2009-114128 A | 5/2009 |
| WO | WO-2010/137302 A1 | 12/2010 |
| WO | WO-2012/050041 A | 4/2012 |
| WO | WO-2013/154080 A1 | 10/2013 |
| WO | WO-2015/163280 A | 10/2015 |
| WO | WO-2016/013633 A | 1/2016 |
| WO | WO-2017/069154 A | 4/2017 |

\* cited by examiner

*Primary Examiner* — Shirley V Gembeh
(74) *Attorney, Agent, or Firm* — Foley & Lardner LLP

(57) ABSTRACT

A compound of formula (I) or a salt thereof:

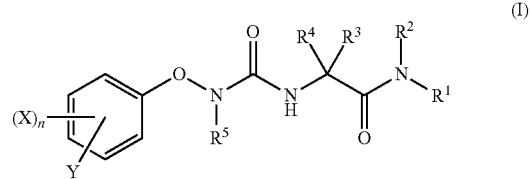

wherein, $R^1$ represents a hydrogen atom, a substituted or unsubstituted $C_{1-6}$ alkyl group and so on; $R^2$ represents a hydrogen atom, or a $C_{1-6}$ alkyl group, $R^3$ and $R^4$ each independently represent a hydrogen atom, or a $C_{1-6}$ alkyl group, $R^5$ represents a substituted or unsubstituted $C_{1-6}$ alkyl group and so on; Y represents a $C_{1-6}$ haloalkyl group, X represents a halogeno group, a $C_{1-6}$ alkyl group and so on; and n represents the number of chemically acceptable groups represented by X and is an integer of 0 to 4, and when n is 2 or more, the groups X is the same as or different from each other.

2 Claims, No Drawings

PHENOXYUREA COMPOUND AND PEST CONTROL AGENT

CROSS-REFERENCE TO RELATED APPLICATIONS

This application is the U.S. National Stage of PCT/JP2019/014798, filed Apr. 3, 2019, which claims priority to JP 2018-074961, filed Apr. 9, 2018.

TECHNICAL FIELD

The present invention relates to a phenoxyurea compound and a pest control agent. More specifically, the present invention relates to a phenoxyurea compound which has excellent insecticidal activity and/or acaricidal activity, and nematicidal activity, is excellent in safety and can be synthesized in an industrially favorable manner; and a pest control agent containing this compound as an active ingredient.

The present application claims priority based on JP2018-074961 that was filed in Japan on Apr. 9, 2018, and the contents thereof are incorporated herein by reference.

BACKGROUND ART

Various compounds having insecticidal/acaricidal activities and nematicidal activity have been proposed. In order to put such a compound to practical use as an agricultural chemical, it is required not only to have sufficiently high efficacy, but also to be difficult to cause drug resistance, not to cause phytotoxicity to plants or soil pollution, and to have low toxicity to livestock and fish, or the like.

Incidentally, Patent Document 1 discloses compounds of formulas (A), (B) and (C), and the like.

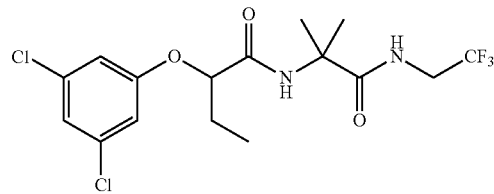

(A)

[0005]

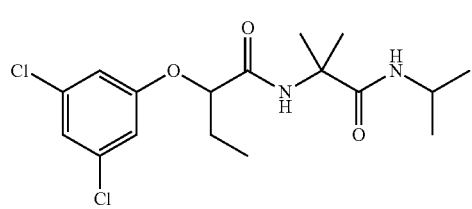

(B)

[0006]

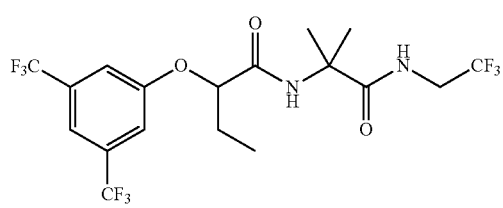

(C)

Patent Documents 2 and 3 disclose compounds of formula (D) and formula (E), and the like.

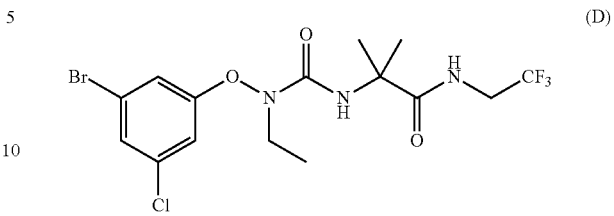

(D)

[0009]

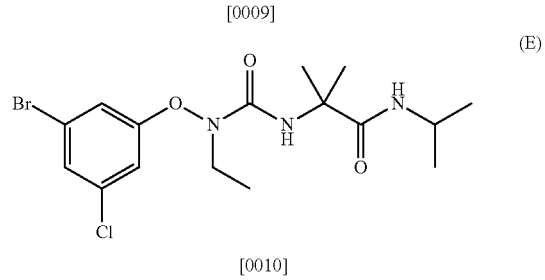

(E)

[0010]

Patent Document 4 discloses a compound of formula (F), and the like.

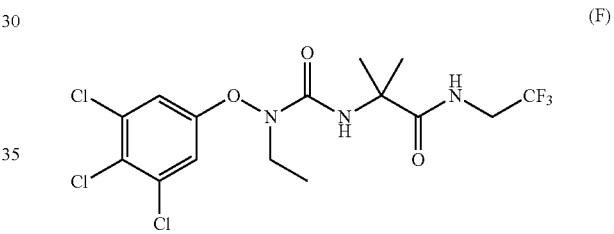

(F)

Further, Patent Document 5 discloses compounds of formula (G) and formula (H), and the like.

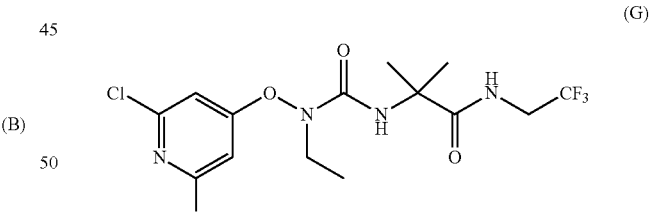

(G)

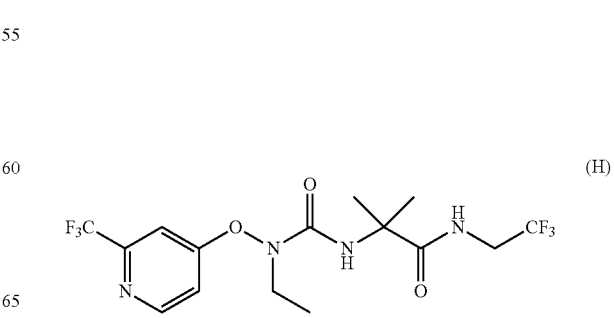

(H)

PRIOR ART DOCUMENTS

Patent Documents

Patent Document 1: Japanese Unexamined Patent Application Publication No. 2009-114128
Patent Document 2: WO2012/050041A
Patent Document 3: WO2015/163280A
Patent Document 4: WO2016/013633A
Patent Document 5: WO2017/069154A

SUMMARY OF THE INVENTION

Problems to be Solved by the Invention

An object of the present invention is to provide a phenoxyurea compound which is excellent in pest control activity such as insecticidal/acaricidal activities and nematicidal activity, excellent in safety and can be synthesized in an industrially favorable manner; and a pest control agent containing this compound as an active ingredient.

Means for Solving the Problem

As a result of intensive studies in order to solve the above problems, the present invention including the following embodiments has been completed.

[1] A compound of formula (I) or a salt thereof:

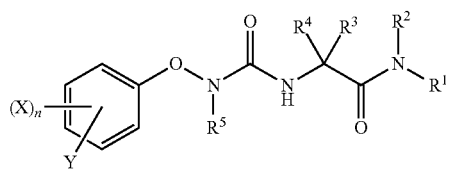

(In the formula (I), $R^1$ represents a hydrogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-8}$ cycloalkyl group or a substituted or unsubstituted $C_{6-10}$ aryl group, $R^2$ represents a hydrogen atom or a $C_{1-6}$ alkyl group, $R^1$ and $R^2$ can form a $C_{2-6}$ alkylene group together, $R^3$ and $R^4$ each independently represent a hydrogen atom or a $C_{1-6}$ alkyl group, $R^5$ represents a substituted or unsubstituted $C_{1-6}$ alkyl group, or a substituted or unsubstituted $C_{2-6}$ alkynyl group, Y represents a $C_{1-6}$ haloalkyl group, X represents a halogeno group, a $C_{1-6}$ alkyl group or a $C_{1-6}$ haloalkyl group, and n represents the number of chemically acceptable groups represented by X and is an integer of 0 to 4, and when n is 2 or more, the groups X is the same or different from each other.)

[2] A compound of formula (II) or formula (III) or a salt thereof.

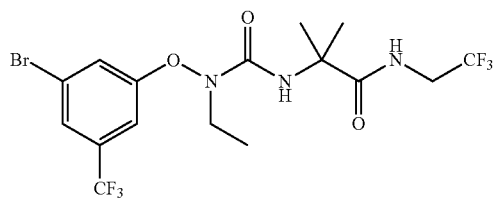

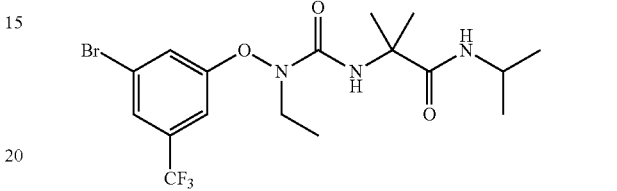

[3] A pest control agent containing at least one selected from the group consisting of the compound according to the above [1] or [2] and salts thereof as an active ingredient.

[4] An insecticidal or acaricidal agent containing at least one selected from the group consisting of the compounds according to the above [1] or [2] and salts thereof as an active ingredient.

[5] A nematicide containing at least one selected from the group consisting of the compounds according to the above [1] or [2] and salts thereof as an active ingredient.

[6] An endoparasite control or extermination agent containing at least one selected from the group consisting of the compounds according to the above [1] or [2] and salts thereof as an active ingredient.

[7] An ectoparasite control agent containing at least one selected from the group consisting of the compounds according to the above [1] or [2] and salts thereof as an active ingredient.

Effect of the Invention

The phenoxyurea compound of the present invention can control pests which are problematic in terms of agricultural crops and hygiene. In particular, agricultural pests, mites and ticks, and nematodes can be effectively controlled at lower concentrations, and acaricide-resistant strains of mites and ticks can be effectively controlled at low concentrations. Furthermore, no phytotoxicity to crops occurs.

Mode of Carrying Out the Invention

The phenoxyurea compound of the present invention is a compound of formula (I) (hereinafter sometimes referred to as a compound (I)) or a salt of the compound (I).

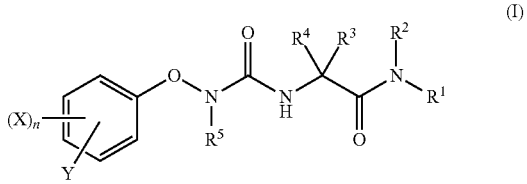

In the present invention, the term "unsubstituted" means that it is composed only of a group which becomes a mother nucleus. When it is described only by the name of the group which becomes the mother nucleus without being described as "substituted", it means "unsubstituted" unless otherwise stated.

On the other hand, the term "substituted" means that any hydrogen atom of a group which becomes a mother nucleus is substituted with a group (substituent) having the same or different structure as that of the mother nucleus. Therefore, a "substituent" is another group bonded to a group which becomes a mother nucleus. The number of substituents may be one, or two or more. The two or more substituents may be the same or different.

The terms "$C_{1-6}$" and the like mean that the number of carbon atoms in the group which becomes a mother nucleus is 1 to 6, and so on. The number of carbon atoms does not include the number of carbon atoms present in the substituent. For example, a butyl group having an ethoxy group as a substituent is classified into a C2 alkoxy C4 alkyl group.

A "substituent" is not particularly limited as long as it is chemically acceptable and has the effects of the present invention. Hereinafter, groups which can be a "substituent" are exemplified.

a $C_{1-6}$ alkyl group such as a methyl group, an ethyl group, an n-propyl group, an i-propyl group, an n-butyl group, an s-butyl group, an i-butyl group, a t-butyl group, an n-pentyl group, and an n-hexyl group;

a $C_{2-6}$ alkenyl group such as a vinyl group, a 1-propenyl group, a 2-propenyl group (allyl group), a 1-butenyl group, a 2-butenyl group, a 3-butenyl group, a 1-methyl-2-propenyl group, and a 2-methyl-2-propenyl group;

a $C_{2-6}$ alkynyl group such as an ethynyl group, a 1-propynyl group, a 2-propynyl group, a 1-butynyl group, a 2-butynyl group, a 3-butynyl group, and a 1-methyl-2-propynyl group;

a $C_{3-8}$ cycloalkyl group such as a cyclopropyl group, a cyclobutyl group, a cyclopentyl group, a cyclohexyl group, and a cubanyl group;

a $C_{6-10}$ aryl group such as a phenyl group and a naphthyl group;

a $C_{6-10}$ aryl $C_{1-6}$ alkyl group such as a benzyl group and a phenethyl group;

a 3- to 6-membered heterocyclyl group;

a 3- to 6-membered heterocyclyl $C_{1-6}$ alkyl group;

a hydroxy group;

a $C_{1-6}$ alkoxy group such as a methoxy group, an ethoxy group, an n-propoxy group, an i-propoxy group, an n-butoxy group, an s-butoxy group, an i-butoxy group, and a t-butoxy group;

a $C_{2-6}$ alkenyloxy group such as a vinyloxy group, an allyloxy group, a propenyloxy group, and a butenyloxy group;

a $C_{2-6}$ alkynyloxy group such as an ethynyloxy group and a propargyloxy group;

a $C_{6-10}$ aryloxy group such as a phenoxy group and a naphthoxy group;

a $C_{6-10}$ aryl $C_{1-6}$ alkoxy group such as a benzyloxy group and a phenethyloxy group;

a 5- to 6-membered heteroaryloxy group such as a thiazolyloxy group and a pyridyloxy group;

a 5- to 6-membered heteroaryl $C_{1-6}$ alkyloxy group such as a thiazolylmethyloxy group and a pyridylmethyloxy group;

a formyl group;

a $C_{1-6}$ alkylcarbonyl group such as an acetyl group and a propionyl group;

a formyloxy group;

a $C_{1-6}$ alkylcarbonyloxy group such as an acetyloxy group and a propionyloxy group;

a $C_{6-10}$ arylcarbonyl group such as a benzoyl group;

a $C_{1-6}$ alkoxycarbonyl group such as a methoxycarbonyl group, an ethoxycarbonyl group, an n-propoxycarbonyl group, an i-propoxycarbonyl group, an n-butoxycarbonyl group and a t-butoxycarbonyl group;

a $C_{1-6}$ alkoxycarbonyloxy group such as a methoxycarbonyloxy group, an ethoxycarbonyloxy group, an n-propoxycarbonyloxy group, an i-propoxycarbonyloxy group, an n-butoxycarbonyloxy group and a t-butoxycarbonyloxy group;

a carboxyl group;

a halogeno group such as a fluoro group, a chloro group, a bromo group, and an iodo group;

a $C_{1-6}$ haloalkyl group such as a chloromethyl group, a chloroethyl group, a trifluoromethyl group, a 1,2-dichloro-n-propyl group, a 1-fluoro-n-butyl group and a perfluoro-n-pentyl group;

a $C_{2-6}$ haloalkenyl group such as a 2-chloro-1-propenyl group and a 2-fluoro-1-butenyl group;

a $C_{2-6}$ haloalkynyl group such as a 4,4-dichloro-1-butynyl group, a 4-fluoro-1-pentynyl group, and a 5-bromo-2-pentynyl group;

a $C_{1-6}$ haloalkoxy group such as a trifluoromethoxy group, a 2-chloro-n-propoxy group, and a 2,3-dichlorobutoxy group;

a $C_{2-6}$ haloalkenyloxy group such as a 2-chloropropenyloxy group and a 3-bromobutenyloxy group;

a $C_{1-6}$ haloalkylcarbonyl group such as a chloroacetyl group, a trifluoroacetyl group and a trichloroacetyl group;

an amino group;

a $C_{1-6}$ alkyl-substituted amino group such as a methylamino group, a dimethylamino group and a diethylamino group;

a $C_{6-10}$ arylamino group such as an anilino group and a naphthylamino group;

a $C_{6-10}$ aryl $C_{1-6}$ alkylamino group such as a benzylamino group and a phenethylamino group;

a formylamino group;

a $C_{1-6}$ alkylcarbonylamino group such as an acetylamino group, a propanoylamino group, a butyrylamino group and an i-propylcarbonylamino group;

a $C_{1-6}$ alkoxycarbonylamino group such as a methoxycarbonylamino group, an ethoxycarbonylamino group, an n-propoxycarbonylamino group and an i-propoxycarbonylamino group;

an unsubstituted or substituted aminocarbonyl group such as an aminocarbonyl group, a dimethylaminocarbonyl group, a phenylaminocarbonyl group, an N-phenyl-N-methylaminocarbonyl group and a 2,2,2-trifluoroethylaminocarbonyl group;

an imino $C_{1-6}$ alkyl group such as an iminomethyl group, a (1-imino)ethyl group and a (1-imino)-n-propyl group;

a substituted or unsubstituted N-hydroxyimino $C_{1-6}$ alkyl group such as an N-hydroxy-iminomethyl group, a (1-(N-hydroxy)-imino)ethyl group, a (1-(N-hydroxy)-imino)propyl group, an N-methoxy-iminomethyl group, and a (1-(N-methoxy)-imino)ethyl group;

an aminocarbonyloxy group;

a $C_{1-6}$ alkyl-substituted aminocarbonyloxy group such as an ethylaminocarbonyloxy group, and a dimethylaminocarbonyloxy group;

a mercapto group;

a $C_{1-6}$ alkylthio group such as a methylthio group, an ethylthio group, an n-propylthio group, an i-propylthio group, an n-butylthio group, an i-butylthio group, an s-butylthio group and a t-butylthio group;

a C$_{1-6}$ haloalkylthio group such as a trifluoromethylthio group and a 2,2,2-trifluoroethylthio group;

a C$_{6-10}$ arylthio group such as a phenylthio group and a naphthylthio group; a 5- to 6-membered heteroarylthio group such as a thiazolylthio group and a pyridylthio group;

a C$_{1-6}$ alkylsulfinyl group such as a methylsulfinyl group, an ethylsulfinyl group and a t-butylsulfinyl group;

a C$_{1-6}$ haloalkylsulfinyl group such as a trifluoromethylsulfinyl group and a 2,2,2-trifluoroethylsulfinyl group;

a C$_{6-10}$ arylsulfinyl group such as a phenylsulfinyl group;

a 5- to 6-membered heteroarylsulfinyl group such as a thiazolylsulfinyl group and a pyridylsulfinyl group;

a C$_{1-6}$ alkylsulfonyl group such as a methylsulfonyl group, an ethylsulfonyl group and a t-butylsulfonyl group;

a C$_{1-6}$ haloalkylsulfonyl group such as a trifluoromethylsulfonyl group and a 2,2,2-trifluoroethylsulfonyl group;

a C$_{6-10}$ arylsulfonyl group such as a phenylsulfonyl group;

a 5- to 6-membered heteroarylsulfonyl group such as a thiazolylsulfonyl group and a pyridylsulfonyl group;

a C$_{1-6}$ alkylsulfonyloxy group such as a methylsulfonyloxy group, an ethylsulfonyloxy group and a t-butylsulfonyloxy group;

a C$_{1-6}$ haloalkylsulfonyloxy group such as a trifluoromethylsulfonyloxy group and a 2,2,2-trifluoroethylsulfonyloxy group;

a tri C$_{1-6}$ alkyl-substituted silyl group such as a trimethylsilyl group, a triethylsilyl group and a t-butyldimethylsilyl group;

a tri C$_{6-10}$ aryl-substituted silyl group such as a triphenylsilyl group;

a cyano group; a nitro group.

Further, in these "substituents", any hydrogen atom in the substituent may be substituted with a group having a different structure. Examples of the "substituent" in this case include a C$_{1-6}$ alkyl group, a C$_{1-6}$ haloalkyl group, a C$_{1-6}$ alkoxy group, a C$_{1-6}$ haloalkoxy group, a halogeno group, a cyano group and a nitro group.

Further, the above-described "3- to 6-membered heterocyclyl group" includes 1 to 4 hetero atoms selected from the group consisting of a nitrogen atom, an oxygen atom and a sulfur atom as constituent atoms of the ring. The heterocyclyl group may be either monocyclic or polycyclic. As long as the polycyclic heterocyclyl group includes at least one heterocyclic ring, the remaining ring may be any of a saturated alicyclic ring, an unsaturated alicyclic ring or an aromatic ring. Examples of the "3- to 6-membered heterocyclyl group" include a 3- to 6-membered saturated heterocyclyl group, a 5- to 6-membered heteroaryl group, and a 5- to 6-membered partially unsaturated heterocyclyl group.

Examples of the 3- to 6-membered saturated heterocyclyl group include an aziridinyl group, an epoxy group, a pyrrolidinyl group, a tetrahydrofuranyl group, a thiazolidinyl group, a piperidyl group, a piperazinyl group, a morpholinyl group, a dioxolanyl group, and a dioxanyl group.

Examples of the 5-membered heteroaryl group include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group and a tetrazolyl group.

Examples of the 6-membered heteroaryl group include a pyridyl group, a pyrazinyl group, a pyrimidinyl group, a pyridazinyl group and a triazinyl group.

In the formula (I), R$^1$ represents a hydrogen atom, a substituted or unsubstituted C$_{1-6}$ alkyl group, a substituted or unsubstituted C$_{2-6}$ alkenyl group, a substituted or unsubstituted C$_{2-6}$ alkynyl group, a substituted or unsubstituted C$_{3-8}$ cycloalkyl group or a substituted or unsubstituted C$_{6-10}$ aryl group.

The "C$_{1-6}$ alkyl group" represented by R$^1$ may be linear or branched. Examples of the alkyl group include a methyl group, an ethyl group, an n-propyl group, an n-butyl group, an n-pentyl group, an n-hexyl group, an i-propyl group, an i-butyl group, an s-butyl group, a t-butyl group, an i-pentyl group, a neopentyl group, a 2-methylbutyl group, a 2,2-dimethylpropyl group and an i-hexyl group.

Specific examples of "C$_{1-6}$ alkyl group having a substituent" include a C$_{1-6}$ haloalkyl group such as a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 1-chloroethyl group, a 2,2-difluoroethyl group, a 2,2,2-trifluoroethyl group, a 2-chloro-2,2-difluoroethyl group, a 2,2,2-trichloroethyl group, a pentafluoroethyl group, a 3,3,3-trifluoropropyl group, a 2,2,3,3,3-pentafluoropropyl group, a 4-fluorobutyl group, a 2,2,3,3,4,4,4-heptafluorobutyl group, a 4-chlorobutyl group, a 2,2,2-trifluoro-1-trifluoromethylethyl group, a 1,1,1,3,3,3-hexafluoropropan-2-yl group, a perfluoropropan-2-yl group, a perfluorohexyl group, a perchlorohexyl group and a 2,4,6-trichlorohexyl group;

a C$_{3-8}$ cycloalkyl C$_{1-6}$ alkyl group such as a cyclopropylmethyl group, a 2-cyclopropylethyl group, a cyclopentylmethyl group, a 2-cyclohexylethyl group and a 2-cyclooctylethyl group;

a cyano C$_{1-6}$ alkyl group such as a cyanomethyl group;

a C$_{1-6}$ alkoxycarbonyl C$_{1-6}$ alkyl group such as an ethoxycarbonylmethyl group;

a substituted or unsubstituted aminocarbonyl C$_{1-6}$ alkyl group (preferably, a C$_{1-6}$ haloalkylaminocarbonyl C$_{1-6}$ alkyl group) such as a 2,2,2-trifluoroethylaminocarbonylmethyl group; and a C$_{1-6}$ alkylthio C$_{1-6}$ alkyl group such as a 2-(methylthio)ethyl group.

Preferred examples of the substituent on the "C$_{1-6}$ alkyl group" represented by R$^1$ include a halogeno group such as a fluoro group, a chloro group, a bromo group and an iodo group; a C$_{1-6}$ alkoxycarbonyl group such as a methoxycarbonyl group, an ethoxycarbonyl group, an n-propoxycarbonyl group, an i-propoxycarbonyl group, an n-butoxycarbonyl group and a t-butoxycarbonyl group; a substituted or unsubstituted aminocarbonyl group (preferably a C$_{1-6}$ haloalkylaminocarbonyl group) such as a 2,2,2-trifluoroethylaminocarbonyl group; a C$_{1-6}$ alkylthio group such as a methylthio group, an ethylthio group, an n-propylthio group, an i-propylthio group, an n-butylthio group, an i-butylthio group, an s-butylthio group and a t-butylthio group; a C$_{3-8}$ cycloalkyl group such as a cyclopropyl group, a cyclobutyl group, a cyclopentyl group, a cyclohexyl group and a cubanyl group; and a cyano group.

Examples of the "C$_{2-6}$ alkenyl group" represented by R$^1$ include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group and a 5-hexenyl group.

Examples of the "C$_{2-6}$ alkynyl group" represented by R$^1$ include an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group and a 1,1-dimethyl-2-butynyl group.

Preferred examples of the substituent on the "$C_{2-6}$ alkenyl group" and the "$C_{2-6}$ alkynyl group" represented by $R^1$ include a halogeno group such as a fluoro group, a chloro group, a bromo group and an iodo group; and a cyano group.

Examples of the "$C_{3-8}$ cycloalkyl group" represented by $R^1$ include a cyclopropyl group, a cyclobutyl group, a cyclopentyl group and a cyclohexyl group.

The "$C_{6-10}$ aryl group" represented by $R^1$ is a group formed by eliminating one hydrogen on the ring of a monocyclic or polycyclic aromatic hydrocarbon. Examples of the "$C_{6-10}$ aryl group" include a phenyl group and a naphthyl group.

Preferred examples of the substituent on the "$C_{3-8}$ cycloalkyl group" and the "$C_{6-10}$ aryl group" represented by $R^1$ include a halogeno group such as a fluoro group, a chloro group, a bromo group and an iodo group; a $C_{1-6}$ haloalkyl group such as a trifluoromethyl group, a 2,2,2-trifluoroethyl group and a perfluoroethyl group; and a cyano group.

In the formula (I), $R^2$ represents a hydrogen atom or a $C_{1-6}$ alkyl group.

As the "$C_{1-6}$ alkyl group" represented by $R^2$, the same as those specifically exemplified for $R^1$ can be mentioned.

$R^1$ and $R^2$ may form a $C_{2-6}$ alkylene group together.

Examples of the "$C_{2-6}$ alkylene group" formed by $R^1$ and $R^2$ together include an ethylene group, a propane-1,3-diyl group (also known as a trimethylene group), a propane-1,2-diyl group (also known as a propylene group), a butane-1,4-diyl group, a butane-1,3-diyl group, a butane-1,2-diyl group and a pentane-1,5-diyl group.

In the formula (I), $R^3$ and $R^4$ each independently represent a hydrogen atom or a $C_{1-6}$ alkyl group.

As the "$C_{1-6}$ alkyl group" represented by $R^3$ and $R^4$, the same as those specifically exemplified for $R^1$ can be mentioned.

In the formula (I), $R^5$ represents a substituted or unsubstituted $C_{1-6}$ alkyl group, or a substituted or unsubstituted $C_{2-6}$ alkynyl group.

As the "substituted or unsubstituted $C_{1-6}$ alkyl group" and the "substituted $C_{2-6}$ alkynyl group" represented by $R^5$, the same as those specifically exemplified for $R^1$ can be mentioned.

In the formula (I), Y represents a $C_{1-6}$ haloalkyl group.

As the "$C_{1-6}$ haloalkyl group" represented by Y, the same as those specifically exemplified for $R^1$ can be mentioned.

In the formula (I), X represents a halogeno group, a $C_{1-6}$ alkyl group or a $C_{1-6}$ haloalkyl group.

As the "halogeno group" represented by X, a fluoro group, a chloro group, a bromo group, an iodo group and the like can be mentioned.

As the "$C_{1-6}$ alkyl group" and the "$C_{1-6}$ haloalkyl group" represented by X, the same as those specifically exemplified for $R^1$ can be mentioned.

In the formula (I), n represents the number of chemically acceptable groups represented by X, and is an integer of 0 to 4. When n is 2 or more, the groups X may be the same or different from each other.

Preferred examples of the phenoxyurea compound of the present invention include a compound of formula (II) (hereinafter sometimes referred to as compound (II)), and a compound of formula (III) (hereinafter sometimes referred to as compound (III)).

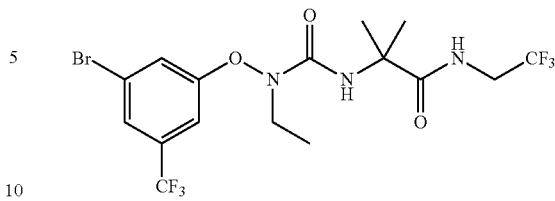

(II)

The compound (II) can take two crystal forms within ordinary condition ranges of temperature, pressure and the like. That is, the compound (II) includes high melting point crystals having a melting point of 121 to 122° C. and low melting point crystals having a melting point of 113 to 114° C.

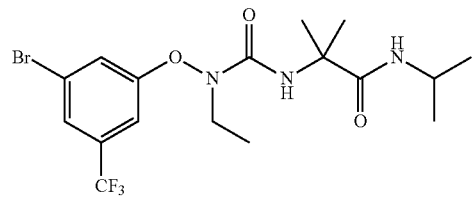 [SMILES: CCN(Oc1cc(Br)cc(C(F)(F)F)c1)C(=O)NC(C)(C)C(=O)NC(C)C]

(III)

The phenoxyurea compound of the present invention is particularly preferably a compound of formula (II).

The compound (III) may form a 0.5 hydrate in some cases. The melting point of the 0.5 hydrate of the compound (III) is from 91 to 95° C.

The salt of compound (I), (II) or (III) is not particularly limited as long as it is an agriculturally and horticulturally acceptable salt. Examples thereof include salts of inorganic acids such as hydrochloric acid and sulfuric acid; salts of organic acids such as acetic acid and lactic acid; salts of alkali metals such as lithium, sodium and potassium; salts of alkaline earth metals such as calcium and magnesium; salts of transition metals such as iron and copper; and salts of organic bases such as ammonia, triethylamine, tributylamine, pyridine and hydrazine.

The compound (I), (II) or (III) or a salt thereof is not particularly limited by its production method. Further, a salt of the compound (I), (II) or (III) can be obtained from the compound (I), (II) or (III) by a known method. For example, the compound (I), (II) or (III) or the salt thereof of the present invention can be obtained by a known production method described in the Examples and the like.

The phenoxyurea compound of the present invention can be produced, for example, by the methods shown below.

(Synthesis method 1)

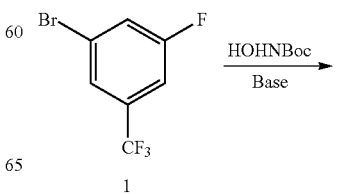

1

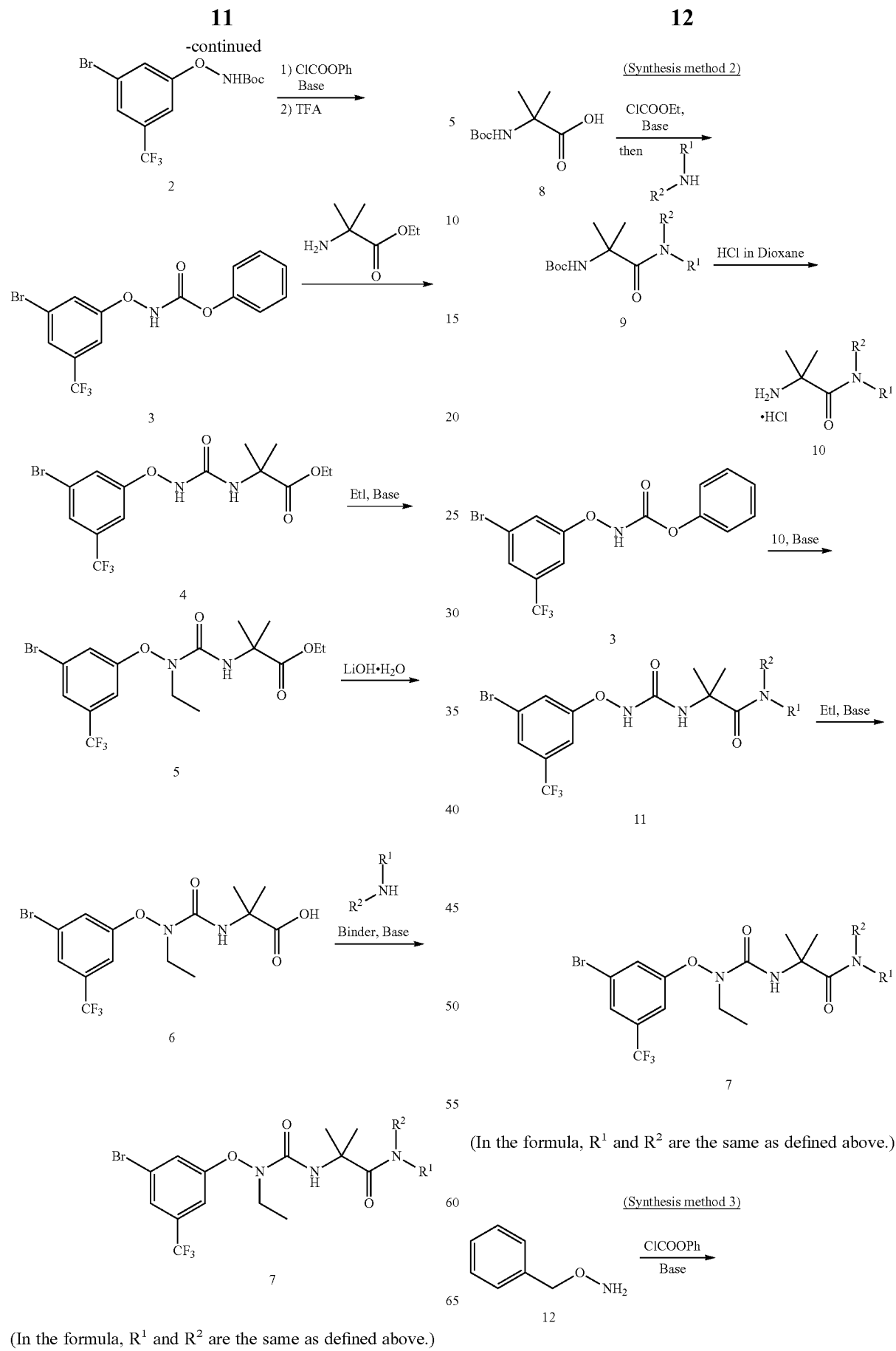

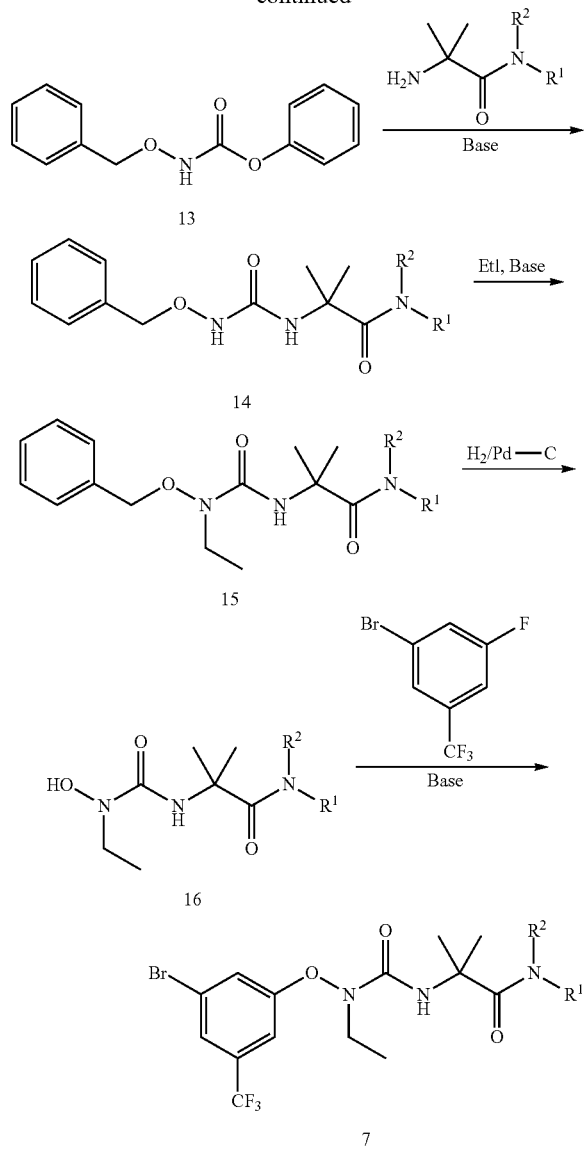

(In the formula, $R^1$ and $R^2$ are the same as defined above.)

The phenoxyurea compound of the present invention is excellent in the effect of controlling harmful organisms such as various agricultural pests, mites and ticks and nematodes which affect the growth of plants.

In addition, the phenoxyurea compound of the present invention is a highly safe compound because it has no phytotoxicity to crops and has low toxicity to fish and warm-blooded animals. Therefore, it is useful as an active ingredient of an insecticide, acaricide or nematicide.

Furthermore, in recent years, resistance to various existing drugs has developed in a number of insect pests such as diamondback moths, planthoppers, leafhoppers and aphids, causing problems of insufficient efficacy of these drugs, and drugs that are effective even against the resistant strains of insect pests have been desired. The phenoxyurea compound of the present invention exhibits excellent control effects not only on susceptible strains, but also on various resistant strains of insect pests and acaricide-resistant strains of mites and ticks.

The phenoxyurea compound of the present invention is excellent in the effect of controlling endoparasites which harm humans and animals. In addition, it is a highly safe compound because of its low toxicity to fish and warm-blooded animals. Therefore, it is useful as an active ingredient of an endoparasite control agent.

In addition, the phenoxyurea compound of the present invention shows efficacy in all developmental stages of the organisms to be controlled, and shows excellent control effects, for example, on eggs, nymphs, larvae, pupae and adults of mites and ticks, insects and the like.

[Pest Control Agent]

The pest control agent of the present invention contains at least one selected from the phenoxyurea compounds of the present invention as an active ingredient. The amount of the phenoxyurea compound contained in the pest control agent of the present invention is not particularly limited as long as the pest control effects are exhibited. The pest control agent is an agent for controlling pests, and includes an insecticide or acaricide, a nematicide, an endoparasite control agent (endoparasiticide) or extermination agent, an ectoparasite control agent (ectoparasiticide), and the like.

[Insecticide, Acaricide or Nematicide]

The insecticide, acaricide or nematicide of the present invention contains at least one selected from the phenoxyurea compounds of the present invention as an active ingredient. The amount of the phenoxyurea compound of the present invention contained in the insecticide, acaricide or nematicide of the present invention is not particularly limited as long as the pest control effects are exhibited.

Examples of plants to which the insecticide, acaricide or nematicide of the present invention can be applied include grains, vegetables, root vegetables, potatoes, trees, pasture grasses and turf grasses.

Further, the insecticide, acaricide or nematicide of the present invention is not particularly limited by the species of the plant to which it is applied. Examples of the plant species include an original species, a variant species, an improved variety, a cultivar, a mutant, a hybrid and a genetically modified organism (GMO).

The insecticide, acaricide or nematicide of the present invention can be applied to each portion of these plants, for example, leaves, stems, stalks, flowers, buds, fruits, seeds, sprouts, roots, tubers, tuberous roots, shoots, cuttings and the like. In addition, improved varieties and variant species, cultivars, mutants, hybrids and genetically modified organisms (GMOs) of these plants can also be subjected to treatments.

The following are examples of plants to which the application is useful.

(1) Plants of the family Malvaceae such as *Abelmoschus esculentus* and *Gossypium hirsutum*;

(2) plants of the family Sterculiaceae such as *Theobroma cacao*;

(3) plants of the family Chenopodiaceae such as *Beta vulgaris, Beta vulgaris* var. *cicla* L., *Spinacia oleracea*;

(4) plants of the family Rubiaceae such as *Coffea* spp;

(5) plants of the family Cannabaceae such as *Humulus lupulus*;

(6) plants of the family Cruciferae such as *Brassica cempestris, Brassica juncea, Brassica juncea* var. *integrifolia, Brassica napus, Brassica oleracea* var. *botrytis, Brassica oleracea* var. *capitata, Brassica oleracea* var. *italica, Brassica rapa, Brassica rapa* var. *chinensis, Brassica rapa* var. *glabra, Brassica rapa* var. *hakabura, Brassica rapa* var. *lancinifolia, Capsella bursa-pastoris, Nasturtium* spp., *Raphanus sativus, Wasabia japonica*;

(7) plants of the family Linaceae such as *Linaceae usitatissimum*;

(8) plants of the family Gramineae such as *Avena sativa, Coix lacryma-jobi* var. *ma-yuen, Dactylis glomerata, Hordeum vulgare, Oryza sativa, Phleum pratense, Saccharum officinarum, Secale cereale, Setaria italica, Triticum aestivum, Zea meys, Zoysia* spp.;

(9) plants of the family Cucurbitaceae such as *Benincasa hispida, Citrulus lanatus, Cucurbita maxima, Cucurbita moschata, Cucurbita pepo, Lagenaria siceraria, Luffa cylindrica*;

(10) plants of the family Anacardiaceae such as *Anacardium, Mangifera*;

(11) plants of the family Ebenaceae such as *Diospyros kaki*;

(12) plants of the family Betulaceae such as *Corylus avellana*;

(13) plants of the family Compositae such as *Artemisia indica* var. *maximowiczii, Arctium lappa* L., *Cichorium intybus, Cynara scolymus, Glebionis coronaria, Helianthus annuus, Lactuca sativa*;

(14) plants of the family Asparagaceae such as *Asparagus officinalis* L.;

(15) plants of the family Moraceae such as *Ficus carica* L.;

(16) plants of the family Juglandaceae such as *Juglans* spp.;

(17) plants of the family Pedaliaceae such as *Sesamum indicum*;

(18) plants of the family Piperaceae such as *Piper nigrum*;

(19) plants of the family Araceae such as *Amorphophallus rivieri* var. *Konjac, Colocasia esculenta*;

(20) plants of the family Lamiaceae such as Mentha spp., *Ocimum basilicum, Perilla frutescens* var. *crispa, Salvia officinalis*;

(21) plants of the family Zingiberaceae such as *Curcuma longa, Hedychium* spp., *Zingiber mioga*;

(22) plants of the family Umbelliferae such as *Apium graveolens* L., *Daucus carota* var. *sativa, Oenanthe javanica, Osmunda japonica* Thunb, *Petroselium crispum*;

(23) plants of the family Grossulariaceae such as *Ribes uva-crispa*;

(24) plants of the family Polygonaceae such as *Fagopyrum esculentum*);

(25) plants of the family Ericaceae such as *Vaccinium* spp;

(26) plants of the family Theaceae such as *Camellia sinensis*);

(27) plants of the family Solanaceae such as *Capsicum annuum, Capsicum annuum* var. *'grossum', Lycopersicon esculentum, Nicotiana tabacum, Solanum melongena, Solanum tuberosum*;

(28) plants of the family Bromeliaceae such as *Ananas comosus*;

(29) plants of the family Musaceae such as *Musa* spp.;

(30) plants of the family Nelumbonaceae such as *Nelumbo nucifera*;

(31) plants of the family Caricaceae such as *Carica papaya*;

(32) plants of the family Rosaceae such as *Chaenomeles sinensis, Eriobotrya japonica* Lindl., *Fragaria* spp., *Malus pumila, Prunus armeniaca, Prunus avium, Prunus cerasus, Prunus dulcis, Prunus mume, Prunus persica, Prunus salicina, Pyrus pyrifolia* var. *culta, Pyrus communis, Rubus* spp.;

(33) plants of the family Convolvulaceae such as *Ipomoea batatas* Lam. var. *edulis* Makino;

(34) plants of the family Vitaceae such as *Vitis* spp.;

(35) plants of the family Fagaceae such as *Castanea crenata* Sieb. Et Zucc.;

(36) plants of the family Actinidiaceae such as *Actinidia deliciosa*;

(37) plants of the family Leguminosae such as *Arachis hypogaea, Glycine max* subsp. *max, Glycine max* subsp. *soja, Lens culinaris, Medicago sativa, Pisum sativum* L., *Phaseolus vulgaris, Vicia angustifolia, Vicia faba, Vigna angularis*;

(38) plants of the family Rutaceae such as *Citrus junos, Citrus kinokuni, Citrus limon, Citrus sinensis, Citrus unshiu, Citrus×paradisi, Fortunella japonica, Zanthoxylum piperitum*;

(39) plants of the family Oleaceae such as *Jasminum* spp., *Olea europaea*;

(40) plants of the family Dioscoreaceae such as *Dioscorea japonica* Thunb., *Dioscorea batatas*;

(41) plants of the family Liliaceae such as *Allium cepa, Allium fistulosum, Allium sativum, Allium schoenoprasum, Allium tuberosum, Tulipa gesneriana*;

The insecticide, acaricide or nematicide of the present invention does not cause phytotoxicity to the above-mentioned plants.

The insecticide, acaricide or nematicide of the present invention is preferably used for grains; vegetables; root vegetables; potatoes; flowers and ornamental plants; fruit trees; trees of foliage plants, tea, coffee, cacao and the like; pasture grasses; turf grasses; and plants such as cotton.

The insecticide, acaricide or nematicide of the present invention can be used for seed treatment, foliage application, soil application, water surface application and the like, in order to control various agricultural pests, mites and ticks, and nematodes.

Specific examples of various agricultural pests, mites and ticks, and nematodes which can be controlled by the insecticide, acaricide or nematicide of the present invention are shown below.

(1) Butterflies or Moths of the Order Lepidoptera (a) Moths of the family Arctiidae such as *Hyphantria cunea* and *Lemyra imparilis*;

(b) moths of the family Bucculatricidae such as *Bucculatrix pyrivorella*;

(c) moths of the family Carposinidae such as *Carposina sasakii*;

(d) moths of the family Crambidae, for example, species belonging to the genus *Diaphania* (*Diaphania* spp.) such as *Diaphania indica* and *Diaphania nitidalis*; for example, species belonging to the genus *Ostrinia* (*Ostrinia* spp.) such as *Ostrinia furnacalis, Ostrinia nubilalis* and *Ostrinia scapulalis*; and others such as *Chilo suppressalis, Cnaphalocrocis medinalis, Conogethes punctiferalis, Diatraea grandiosella, Glyphodes pyloalis, Hellula undalis* and *Parapediasia teterrella*;

(e) moths of the family Gelechiidae such as *Helcystogramma triannulella, Pectinophora gossypiella, Phthorimaea operculella* and *Sitotroga cerealella*;

(f) moths of the family Geometridae such as *Ascotis selenaria*;

(g) moths of the family Gracillariidae such as *Caloptilia theivora, Phyllocnistis citrella* and *Phyllonorycter ringoniella*;

(h) butterflies of the family Hesperiidae such as *Parnara guttata*;

(i) moths of the family Lasiocampidae such as *Malacosoma neustria*;

(j) moths of the family Lymantriidae, for example, species belonging to the genus *Lymantria* (*Lymantria* spp.) such as

*Lymantria dispar* and *Lymantria monacha*; and others such as *Euproctis pseudoconspersa* and *Orgyia thyellina*;

(k) moths of the family Lyonetiidae, for example, species belonging to the genus *Lyonetia* (*Lyonetia* spp.) such as *Lyonetia clerkella* and *Lyonetia prunifoliella malinella*;

(l) moths of the family Noctuidae, for example, species belonging to the genus *Spodoptera* (*Spodoptera* spp.) such as *Spodoptera depravata*, *Spodoptera eridania*, *Spodoptera exigua*, *Spodoptera frugiperda*, *Spodoptera littoralis* and *Spodoptera litura*; for example, species belonging to the genus *Autographa* (*Autographa* spp.) such as *Autographa gamma* and *Autographa nigrisigna*; for example, species belonging to the genus *Agrotis* (*Agrotis* spp.) such as *Agrotis ipsilon* and *Agrotis segetum*; for example, species belonging to the genus *Helicoverpa* (*Helicoverpa* spp.) such as *Helicoverpa armigera*, *Helicoverpa assulta* and *Helicoverpa zea*; for example, species belonging to the genus *Heliothis* (*Heliothis* spp.) such as *Heliothis armigera* and *Heliothis virescens*; and others such as *Aedia leucomelas*, *Ctenoplusia agnata*, *Eudocima tyrannus*, *Mamestra brassicae*, *Mythimna separata*, *Naranga aenescens*, *Panolis japonica*, *Peridroma saucia*, *Pseudoplusia includens* and *Tritoplusia ni*;

(m) moths of the family Nolidae such as *Earias insulana*;

(n) butterflies of the family Pieridae, for example, species belonging to the genus *Pieris* (*Pieris* spp.) such as *Pieris brassicae* and *Pieris rapae crucivora*;

(o) moths of the family Plutellidae, for example, species belonging to the genus *Acrolepiopsis* (*Acrolepiopsis* spp.) such as *Acrolepiopsis sapporensis* and *Acrolepiopsis suzukiella*; and others such as *Plutella xylostella*;

(p) moths of the family Pyralidae such as *Cadra cautella*, *Elasmopalpus lignosellus*, *Etiella zinckenella* and *Galleria mellonella*;

(q) moths of the family Sphingidae, for example, species belonging to the genus *Manduca* (*Manduca* spp.) such as *Manduca quinquemaculata* and *Manduca sexta*;

(r) moths of the family Stathmopodidae such as *Stathmopoda masinissa*;

(s) moths of the family Tineidae such as *Tinea translucens*;

(t) moths of the family Tortricidae, for example, species belonging to the genus *Adoxophyes* (*Adoxophyes* spp.) such as *Adoxophyes honmai* and *Adoxophyes orana*; for example, species belonging to the genus *Archips* (*Archips* spp.) such as *Archips breviplicanus* and *Archips fuscocupreanus*; and others such as *Choristoneura fumiferana*, *Cydia pomonella*, *Eupoecilia ambiguella*, *Grapholitha molesta*, *Homona magnanima*, *Leguminivora glycinivorella*, *Lobesia botrana*, *Matsumuraeses phaseoli*, *Pandemis heparana* and *Sparganothis pilleriana*; and (u) moths of the family Yponomeutidae such as *Argyresthia conjugella*.

(2) Insect Pests of the Order Thysanoptera (a) pests of the family Phlaeothripidae such as *Ponticulothrips diospyrosi*; and (b) pests of the family Thripidae, for example, species belonging to the genus *Frankliniella* (*Frankliniella* spp.) such as *Frankliniella intonsa* and *Frankliniella occidentalis*; for example, species belonging to the genus *Thrips* (*Thrips* spp.) such as *Thrips palmi* and *Thrips tabaci*; and others such as *Heliothrips haemorrhoidalis* and *Scirtothrips dorsalis*.

(3) Insect Pests of the Order Hemiptera (A) Archaeorrhyncha (a) pests of the family Delphacidae such as *Laodelphax striatella*, *Nilaparvata lugens*, *Perkinsiella saccharicida* and *Sogatella furcifera*.

(B) Clypeorrhyncha (a) pests of the family Cicadellidae, for example, species belonging to the genus *Empoasca* (*Empoasca* spp.) such as *Empoasca fabae*, *Empoasca nipponica*, *Empoasca onukii* and *Empoasca sakaii*; and others such as *Arboridia apicalis*, *Balclutha saltuella*, *Epiacanthus stramineus*, *Macrosteles striifrons* and *Nephotettix cinctinceps*.

(C) Heteroptera (a) pests of the family Alydidae such as *Riptortus clavatus*;

(b) pests of the family Coreidae such as *Cletus punctiger* and *Leptocorisa chinensis*;

(c) pests of the family Lygaeidae such as *Blissus leucopterus*, *Cavelerius saccharivorus* and *Togo hemipterus*;

(d) pests of the family Miridae such as *Halticus insularis*, *Lygus lineolaris*, *Psuedatomoscelis seriatus*, *Stenodema sibiricum*, *Stenotus rubrovittatus* and *Trigonotylus caelestialium*;

(e) pests of the family Pentatomidae, for example, species belonging to the genus *Nezara* (*Nezara* spp.) such as *Nezara antennata* and *Nezara viridula*; for example, species belonging to the genus *Eysarcoris* (*Eysarcoris* spp.) such as *Eysarcoris aeneus*, *Eysarcoris lewisi* and *Eysarcoris ventralis*; and others such as *Dolycoris baccarum*, *Eurydema rugosum*, *Glaucias subpunctatus*, *Halyomorpha halys*, *Piezodorus hybneri*, *Plautia crossota* and *Scotinophora lurida*;

(f) pests of the family Pyrrhocoridae such as *Dysdercus cingulatus*;

(g) pests of the family Rhopalidae such as *Rhopalus msculatus*;

(h) pests of the family Scutelleridae such as *Eurygaster integriceps*; and (i) pests of the family Tingidae such as *Stephanitis nashi*.

(D) Sternorrhyncha (a) pests of the family Adelgidae such as *Adelges laricis*;

(b) pests of the family Aleyrodidae, for example, species belonging to the genus *Bemisia* (*Bemisia* spp.) such as *Bemisia argentifolii* and *Bemisia tabaci*; and others such as *Aleurocanthus spiniferus*, *Dialeurodes citri* and *Trialeurodes vaporariorum*;

(c) pests of the family Aphididae, for example, species belonging to the genus *Aphis* (*Aphis* spp.) such as *Aphis craccivora*, *Aphis fabae*, *Aphis forbesi*, *Aphis gossypii*, *Aphis pomi*, *Aphis sambuci* and *Aphis spiraecola*; for example, species belonging to the genus *Rhopalosiphum* (*Rhopalosiphum* spp.) such as *Rhopalosiphum maidis* and *Rhopalosiphum padi*; for example, species belonging to the genus *Dysaphis* (*Dysaphis* spp.) such as *Dysaphis plantaginea* and *Dysaphis radicola*; for example, species belonging to the genus *Macrosiphum* (*Macrosiphum* spp.) such as *Macrosiphum avenae* and *Macrosiphum euphorbiae*; for example, species belonging to the genus *Myzus* (*Myzus* spp.) such as *Myzus cerasi*, *Myzus persicae* and *Myzus varians*; and others such as *Acyrthosiphon pisum*, *Aulacorthum solani*, *Brachycaudus helichrysi*, *Brevicoryne brassicae*, *Chaetosiphon fragaefolii*, *Hyalopterus pruni*, *Hyperomyzus lactucae*, *Lipaphis erysimi*, *Megoura viciae*, *Metopolophium dirhodum*, *Nasonovia ribis-nigri*, *Phorodonhumuli*, *Schizaphis graminum*, *Sitobion avenae* and *Toxoptera aurantii*;

(d) pests of the family Coccidae, for example, species belonging to the genus *Ceroplastes* (*Ceroplastes* spp.) such as *Ceroplastes ceriferus* and *Ceroplastes rubens*;

(e) pests of the family Diaspididae, for example, species belonging to the genus *Pseudaulacaspis* (*Pseudaulacaspis* spp.) such as *Pseudaulacaspis pentagona* and *Pseudaulacaspis prunicola*; for example, species belonging to the genus *Unaspis* (*Unaspis* spp.) such as *Unaspis euonymi* and *Unaspis yanonensis*; and others such as *Aonidiella aurantii, Comstockaspis perniciosa, Fiorinia theae* and *Pseudaonidia paeoniae*;

(f) pests of the family Margarodidae such as *Drosicha corpulenta* and *Icerya purchasi*;

(g) pests of the family Phylloxeridae such as *Viteus vitifolii*;

(h) pests of the family Pseudococcidae, for example, species belonging to the genus *Planococcus* (*Planococcus* spp.) such as *Planococcus citri* and *Planococcus kuraunhiae*; and others such as *Phenacoccus solani* and *Pseudococcus comstocki*; and (i) pests of the family Psyllidae, for example, species belonging to the genus *Psylla* (*Psylla* spp.) such as *Psylla mali* and *Psylla pyrisuga*; and others such as *Diaphorina citri*.

(4) Insect Pests of the Suborder *Polyphaga*

(a) pests of the family Anobiidae such as *Lasioderma serricorne*;

(b) pests of the family Attelabidae such as *Byctiscus betulae* and *Rhynchites heros*;

(c) pests of the family Bostrichidae such as *Lyctus brunneus*;

(d) pests of the family Brentidae such as *Cylas formicarius*;

(e) pests of the family Buprestidae such as *Agrilus sinuatus*;

(f) pests of the family Cerambycidae such as *Anoplophora malasiaca, Monochamus alternatus, Psacothea hilaris* and *Xylotrechus pyrrhoderus*;

(g) pests of the family Chrysomelidae, for example, species belonging to the genus *Bruchus* (*Bruchus* spp.) such as *Bruchus pisorum* and *Bruchus rufimanus*; for example, species belonging to the genus *Diabrotica* (*Diabrotica* spp.) such as *Diabrotica barberi, Diabrotica undecimpunctata* and *Diabrotica virgifera*; for example, species belonging to the genus *Phyllotreta* (*Phyllotreta* spp.) such as *Phyllotreta nemorum* and *Phyllotreta striolata*; and others such as *Aulacophora femoralis, Callosobruchus chinensis, Cassida nebulosa, Chaetocnema concinna, Leptinotarsa decemlineata, Oulema oryzae* and *Psylliodes angusticollis*;

(h) pests of the family Coccinellidae, for example, species belonging to the genus *Epilachna* (*Epilachna* spp.) such as *Epilachna varivestis* and *Epilachna vigintioctopunctata*;

(i) pests of the family Curculionidae, for example, species belonging to the genus *Anthonomus* (*Anthonomus* spp.) such as *Anthonomus grandis* and *Anthonomus pomorum*; for example, species belonging to the genus *Sitophilus* (*Sitophilus* spp.) such as *Sitophilus granarius* and *Sitophilus zeamais*; and others such as *Echinocnemus squameus, Euscepes postfasciatus, Hylobius abietis, Hypera postica, Lissohoptrus oryzophilus, Otiorhynchus sulcatus, Sitona lineatus* and *Sphenophorus venatus*;

(j) pests of the family Elateridae, for example, species belonging to the genus *Melanotus* (*Melanotus* spp.) such as *Melanotus fortnumi* and *Melanotus tamsuyensis*;

(k) pests of the family Nitidulidae such as *Epuraea domina*;

(l) pests of the family Scarabaeidae, for example, species belonging to the genus *Anomala* (*Anomala* spp.) such as *Anomala cuprea* and *Anomala rufocuprea*; and others such as *Cetonia aurata, Gametis jucunda, Heptophylla picea, Melolontha* and *Popillia japonica*;

(m) pests of the family Scolytidae such as *Ips typographus*;

(n) pests of the family Staphylinidae such as *Paederus fuscipes*;

(o) pests of the family Tenebrionidae such as *Tenebrio molitor* and *Tribolium castaneum*; and (p) pests of the family Trogossitidae such as *Tenebroides mauritanicus*.

(5) Insect Pests of the Order Diptera (A) Brachycera (a) pests of the family Agromyzidae, for example, species belonging to the genus *Liriomyza* (*Liriomyza* spp.) such as *Liriomyza bryoniae, Liriomyza chinensis, Liriomyza sativae* and *Liriomyza trifolii*; and others such as *Chromatomyia horticola* and *Agromyza oryzae*;

(b) pests of the family Anthomyiidae, for example, species belonging to the genus *Delia* (*Delia* spp.) such as *Delia platura* and *Delia radicum*; and others such as *Pegomya cunicularia*;

(c) pests of the family Drosophilidae, for example, species belonging to the genus *Drosophila* (*Drosophila* spp.) such as *Drosophila melanogaster* and *Drosophila suzukii*;

(d) pests of the family Ephydridae such as *Hydrellia griseola*;

(e) pests of the family Psilidae such as *Psila rosae*; and (f) pests of the family Tephritidae, for example, species belonging to the genus *Bactrocera* (*Bactrocera* spp.) such as *Bactrocera cucurbitae* and *Bactrocera dorsalis*; for example, species belonging to the genus *Rhagoletis* (*Rhagoletis* spp.) such as *Rhagoletis cerasi* and *Rhagoletis pomonella*; and others such as *Ceratitis capitata* and *Dacus oleae*.

(B) Nematocera (a) pests of the family Cecidomyiidae such as *Asphondylia yushimai, Contarinia sorghicola, Mayetiola destructor* and *Sitodiplosis mosellana*.

(6) Insect Pests of the Order Orthoptera (a) pests of the family Acrididae, for example, species belonging to the genus *Schistocerca* (*Schistocerca* spp.) such as *Schistocerca americana* and *Schistocerca gregaria*; and others such as *Chortoicetes terminifera, Dociostaurus maroccanus, Locusta migratoria, Locustana pardalina, Nomadacris septemfasciata* and *Oxya yezoensis*;

(b) pests of the family Gryllidae such as *Acheta domestica* and *Teleogryllus emma*;

(c) pests of the family Gryllotalpidae such as *Gryllotalpa orientalis*; and (d) pests of the family Tettigoniidae such as *Tachycines asynamorus*.

(7) Acari (A) Acaridida of the order *Astigmata*

(a) mites of the family Acaridae, for example, species belonging to the genus *Rhizoglyphus* (*Rhizoglyphus* spp.) such as *Rhizoglyphus echinopus* and *Rhizoglyphus robini*; for example, species belonging to the genus *Tyrophagus* (*Tyrophagus* spp.) such as *Tyrophagus neiswanderi, Tyrophagus perniciosus, Tyrophagus putrescentiae* and *Tyrophagus similis*; and others such as *Acarus siro, Aleuroglyphus ovatus* and *Mycetoglyphus fungivorus*;

(B) Actinedida of the order Prostigmata (a) mites of the family Tetranychidae, for example, species belonging to the genus *Bryobia* (*Bryobia* spp.) such as *Bryobia praetiosa* and *Bryobia rubrioculus*; for example, species belonging to the genus *Eotetranychus* (*Eotetranychus* spp.) such as *Eotetranychus asiaticus, Eotetranychus* boreus, *Eotetranychus celtis, Eotetranychus geniculatus, Eotetranychus kankitus, Eotetranychus pruni, Eotetranychus shii, Eotetranychus smithi, Eotetranychus suginamensis* and *Eotetranychus uncatus*; for example, species belonging to the genus *Oligonychus* (*Oligonychus* spp.) such as *Oligonychus hondoensis, Oligonychus ilicis, Oligonychus karamatus, Oligonychus mangiferus, Oligonychus orthius, Oligonychus perseae, Oligonychus pustulosus, Oligonychus shinkajii* and *Oligonychus ununguis*; for example, species belonging to the genus *Panonychus* (*Panonychus* spp.) such as *Panonychus citri, Panonychus mori* and *Panonychus ulmi*; for example, species belonging to the genus *Tetranychus* (*Tetranychus* spp.) such as *Tetranychus cinnabarinus, Tetranychus kanzawai, Tetranychus ludeni, Tetranychus quercivorus, Tetranychus phaselus, Tetranychus urticae, Tetranychus viennensis* and *Tetranychus evansi*; for example, species belonging to the genus *Aponychus* (*Aponychus* spp.) such as *Aponychus corpuzae* and *Aponychus firmianae*; for example, species belonging to the genus *Sasanychus* (*Sasanychus* spp.) such as *Sasanychus akitanus* and *Sasanychus pusillus*; for example, species belonging to the genus *Shizotetranychus* (*Shizotetranychus* spp.) such as *Shizotetranychus celarius, Shizotetranychus longus, Shizotetranychus miscanthi, Shizotetranychus recki* and *Shizotetranychus schizopus*; and others such as *Tetranychina harti, Tuckerella pavoniformis* and *Yezonychus sapporensis*;

(b) mites of the family Tenuipalpidae, for example, species belonging to the genus *Brevipalpus* (*Brevipalpus* spp.) such as *Brevipalpus lewisi, Brevipalpus obovatus, Brevipalpus phoenicis, Brevipalpus russulus* and *Brevipalpus californicus*; for example, species belonging to the genus *Tenuipalpus* (*Tenuipalpus* spp.) such as *Tenuipalpus pacificus* and *Tenuipalpus zhizhilashviliae*; and others such as *Dolichotetranychus floridanus*;

(c) mites of the family Eriophyidae, for example, species belonging to the genus *Aceria* (*Aceria* spp.) such as *Aceria diospyri, Aceria ficus, Aceria japonica, Aceria kuko, Aceria paradianthi, Aceria tiyingi, Aceria tulipae* and *Aceria zoysiea*; for example, species belonging to the genus *Eriophyes* (*Eriophyes* spp.) such as *Eriophyes chibaensis* and *Eriophyes emarginatae*; for example, species belonging to the genus *Aculops* (*Aculops* spp.) such as *Aculops lycopersici* and *Aculops pelekassi*; for example, species belonging to the genus *Aculus* (*Aculus* spp.) such as *Aculus fockeui* and *Aculus schlechtendali*; and others such as *Acaphylla theavagrans, Calacarus carinatus, Colomerus vitis, Calepitrimerus vitis, Epitrimerus pyri, Paraphytoptus kikus, Paracalacarus podocarpi* and *Phyllocotruta citri*;

(d) mites of the family Transonemidae, for example, species belonging to the genus *Tarsonemus* (*Tarsonemus* spp.) such as *Tarsonemus bilobatus* and *Tarsonemus waitei*; and others such as *Phytonemus pallidus* and *Polyphagotarsonemus latus*; and (e) mites of the family Penthaleidae, for example, species belonging to the genus *Penthaleus* (*Penthaleus* spp.) such as *Penthaleus erythrocephalus* and *Penthaleus major*.

(8) Plant Parasitic Nematodes
(A) Tylenchida (a) nematodes of the family Anguinidae, for example, species belonging to the genus *Anguina* (*Anguina* spp.) such as *Anguina funesta* and *Anguina tritici*; and species belonging to the genus *Ditylenchus* (*Ditylenchus* spp.) such as *Ditylenchus destructor, Ditylenchus dipsaci* and *Ditylenchus myceliophagus*;

(b) nematodes of the family Aphelenchoididae, for example, species belonging to the genus *Aphelenchoides* (*Aphelenchoides* spp.) such as *Aphelenchoides besseyi, Aphelenchoides fragariae, Aphelenchoides ritzemabosi* and *Aphelenchoides besseyi*; and species belonging to the genus *Bursaphelenchus* (*Bursaphelenchus* spp.) such as *Bursaphelenchus xylophilus*;

(c) nematodes of the family Belonolaimidae, for example, species belonging to the genus *Belonolaimus* (*Belonolaimus* spp.) such as *Belonolaimus longicaudatus*; and species belonging to the genus *Tylenchorhynchus* (*Tylenchorhynchus* spp.) such as *Tylenchorhynchus claytoni* and *Tylenchorhynchus dubius*;

(d) nematodes of the family Criconematidae such as *Criconema mutabile*;

(e) nematodes of the family Dolichodoridae such as *Dolichodorus mediterraneus*;

(f) nematodes of the family Ecphyadophoridae such as *Ecphyadophora tenuissima*;

(g) nematodes of the family Hemicycliophoridae such as *Loofia thienemanni*;

(h) nematodes of the family Heteroderidae, for example, species belonging to the genus *Globodera* (*Globodera* spp.) such as *Globodera rostochiensis, Globodera pallida* and *Globodera tabacum*; and species belonging to the genus *Heterodera* (*Heterodera* spp.) such as *Heterodera avenae, Heterodera cruciferae, Heterodera glycines, Heterodera schachtii* and *Heterodera trifolii*;

(i) nematodes of the family Hoplolaimidae, for example, species belonging to the genus *Helicotylenchus* (*Helicotylenchus* spp.) such as *Helicotylenchus dihystera* and *Helicotylenchus multicinctus*; species belonging to the genus *Hoplolaimus* (*Hoplolaimus* spp.) such as *Hoplolaimus columbus* and *Hoplolaimus galeatus*; and others such as *Rotylenchus robustus* and *Rotylenchulus reniformis*;

(j) nematodes of the family Meloidogynidae, for example, species belonging to the genus *Meloidogyne* (*Meloidogyne* spp.) such as *Meloidogyne arenaria, Meloidogyne chitwoodi, Meloidogyne hapla, Meloidogyne incognita, Meloidogyne javanica* and *Meloidogyne thamesi*;

(k) nematodes of the family Nothotylenchidae such as *Nothotylenchus acris*;

(l) nematodes of the family Paratylenchidae, for example, species belonging to the genus *Paratylenchus* (*Paratylenchus* spp.) such as *Paratylenchus curvitatus* and *Paratylenchus elachistus*; and (m) nematodes of the family Pratylenchidae, for example, species belonging to the genus *Pratylenchus* (*Pratylenchus* spp.) such as *Pratylenchus brachyurus, Pratylenchus coffeae, Pratylenchus curvitatus, Pratylenchus fallax, Pratylenchus goodeyi, Pratylencus neglectus, Pratylenchus penetrans, Pratylencus scribneri, Pratylenchus vulnus* and *Pratylenchus zeae*; and others such as *Nacobbus aberrans, Radopholus similis, Tylenchulus semipenetrans* and *Radopholus citrophilus*.

(B) Dorylaimida (a) nematodes of the family Longidoridae, for example, species belonging to the genus *Longidorus* (*Longidorus* spp.) such as *Longidorus elongates*; and species belonging to the genus *Xiphinema* (*Xiphinema* spp.) such as *Xiphinema americanum, Xiphinema brevicolle, Xiphinema index* and *Xiphinema diversicaudatum*.

(C) Triplonchida (a) nematodes of the family Trichodoridae such as *Trichodorus primitivus* and *Paratrichodorus minor*.

The insecticide, acaricide or nematicide of the present invention may be mixed with or used in combination with other active ingredients such as fungicides, insecticidal and acaricidal agents, nematicides and soil pesticides; plant regulators, synergists, fertilizers, soil conditioners, animal feeds and the like.

A combination of the compound of the present invention and other active ingredients can be expected to have a synergistic effect on insecticidal and acaricidal activity and nematicidal activity. The synergistic effect can be confirmed by the Colby's formula (Colby, S. R.; Calculating Synergistic and Antagonistic Responses of Herbicide Combinations; Weeds 15, pp. 20-22, 1967) according to a conventional method.

Specific examples of insecticidal/acaricidal agents, nematicides, soil pesticides, anthelmintics and the like which can be mixed with or used in combination with the insecticide, acaricide or nematicide of the present invention are shown below.

(1) Acetylcholinesterase inhibitor:

(a) carbamate-based inhibitors: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylylcarb; fenothiocarb, MIPC, MPMC, MTMC, aldoxycarb, allyxycarb, aminocarb, bufencarb, cloethocarb, metam sodium, promecarb;

(b) Organophosphorus-based inhibitors: acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimphos, temephos, terbufos, tetrachlorvinphos, thiometon, triazophos, trichlorfon, vamidothion; bromophos-ethyl, BRP, carbophenothion, cyanofenphos, CYAP, demeton-S-methyl sulfone, dialifos, dichlofenthion, dioxabenzofos, etrimfos, fensulfothion, flupyrazofos, fonofos, formothion, fosmethilan, isazofos, iodofenphos, methacrifos, pirimiphos-ethyl, phosphocarb, propaphos, prothoate, sulprofos.

(2) GABA-gated chloride channel antagonists: acetoprole, chlordane, endosulfan, ethiprole, fipronil, pyrafluprole, pyriprole; camphechlor, heptachlor, dienochlor.

(3) Sodium channel modulators: acrinathrin, d-cis/trans allethrin, d-trans-allethrin, bifenthrin, bioallethrin, bioallethrin S-cyclopentyl isomers, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R)-isomers], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans isomers], prallethrin, pyrethrum, resmethrin, silafluofen, tefluthrin, tetramethrin [(1R)-isomers], tralomethrin, transfluthrin; allethrin, pyrethrin, pyrethrin I, pyrethrin II, profluthrin, dimefluthrin, bioethanomethrin, biopermethrin, transpermethrin, fenfluthrin, fenpirithrin, flubrocythrinate, flufenprox, metofluthrin, protrifenbute, pyresmethrin, terallethrin.

(4) Nicotinic acetylcholine receptor agonists: acetamiprid, clothianidin, dinotefuran, imidacloprid, nitenpyram, nithiazine, thiacloprid, thiamethoxam, sulfoxaflor, nicotine, flupyradifurone.

(5) Nicotinic acetylcholine receptor allosteric modulators: spinetoram, spinosad.

(6) Chloride channel activators: abamectin, emamectin benzoate, lepimectin, milbemectin; ivermectin, selamectin, doramectin, eprinomectin, moxidectin, milbemycin, milbemycin oxime, nemadectin.

(7) Juvenile hormone analogues: hydroprene, kinoprene, methoprene, fenoxycarb, pyriproxyfen; diofenolan, epofenonane, triprene.

(8) Other nonspecific inhibitors: methyl bromide, chloropicrin, sulfuryl fluoride, borax, tartar emetic.

(9) Homoptera selective antifeedants: flonicamid, pymetrozine, pyrifluquinazon.

(10) Mite growth inhibitors: clofentezine, diflovidazin, hexythiazox, etoxazole.

(11) Insect midgut inner membrane disrupting agents derived from microorganisms: *Bacillus thuringiensis* subsp. *israelensi*, *Bacillus sphaericus*, *Bacillus thuringiensis* subsp. *aizawai*, *Bacillus thuringiensis* subsp. *kurstaki*, *Bacillus thuringiensis* subsp. *tenebrionis*, Bt crop proteins: Cry1Ab, Cry1Ac, Cry1Fa, Cry1A.105, Cry2Ab, Vip3A, mCry3A, Cry3Ab, Cry3Bb, Cry34Ab1/Cry35Ab1.

(12) Mitochondrial ATP biosynthetic enzyme inhibitors: diafenthiuron, azocyclotin, cyhexatin, fenbutatin oxide, propargite, tetradifon.

(13) Oxidative phosphorylation uncouplers: chlorfenapyr, sulfluramid, DNOC; binapacryl, dinobuton, dinocap.

(14) Nicotinic acetylcholine receptor channel blockers: bensultap, cartap hydrochloride; nereistoxin; thiosultap monosodium salt, thiocyclam.

(15) Chitin synthesis inhibitors: bistrifluron, chlorfluazuron, diflubenzuron, flucycloxuron, flufenoxuron, hexaflumuron, lufenuron, novaluron, noviflumuron, teflubenzuron, triflumuron, buprofezin, fluazuron.

(16) Diptera molting disrupting agents: cyromazine.

(17) Molting hormone receptor agonists: chromafenozide, halofenozide, methoxyfenozide, tebufenozide.

(18) Octopamine receptor agonists: amitraz, demiditraz, chlordimeform.

(19) Mitochondrial electron transport system complex III inhibitors: acequinocyl, fluacrypyrim, hydramethylnon.

(20) Mitochondrial electron transport system complex I inhibitors: fenazaquin, fenpyroximate, pyrimidifen, pyridaben, tebufenpyrad, tolfenpyrad, rotenone.

(21) Voltage-dependent sodium channel blockers: indoxacarb, metaflumizone.

(22) Acetyl CoA carboxylase inhibitors: spirodiclofen, spiromesifen, spirotetramat.

(23) Mitochondrial electron transport system complex IV inhibitors: aluminum phosphide, calcium phosphide, phosphine, zinc phosphide, cyanide.

(24) Mitochondrial electron transport complex II inhibitors: cyenopyrafen, cyflumetofen, pyflubumide.

(25) Ryanodine receptor modulators: chlorantraniliprole, cyantraniliprole, flubendiamide, cyclaniliprole, tetraniliprole.

(26) Mixed function oxidase inhibitor compounds: piperonyl butoxide.

(27) Latrophilin receptor agonists: depsipeptide, cyclic depsipeptide, 24-membered cyclic depsipeptide, emodepside.

(28) Other agents (with unknown action mechanisms): azadirachtin, benzoximate, bifenazate, bromopropylate, chinomethionate, cryolite, dicofol, pyridalyl, benclothiaz, sulfur, amidoflumet, 1,3-dichloropropene, DCIP, phenisobromolate, benzomate, metaldehyde, chlorobenzilate, clothiazoben, dicyclanil, fenoxacrim, fentrifanil, flubenzimine, fluphenazine, gossyplure, japonilure, metoxadiazone, petroleum, potassium oleate, tetrasul, triarathene, afidopyropen, flometoquin, flufiprole, fluensulfone, meperfluthrin, tetramethylfluthrin, tralopyril, dimefluthrin, methylneodecanamide, fluralaner, afoxolaner, fluxametamide, 5-[5-(3,5-dichlorophenyl)-5-trifluoromethyl-4,5-dihydroisoxazol-3-yl]-2-(1H-1,2,4-triazol-1-yl) benzonitrile (CAS: 943137-49-3), broflanilide, other meta-diamides.

(29) Anthelmintics:
(a) benzimidazole-based anthelmintics: fenbendazole, albendazole, triclabendazole, oxybendazole, mebendazole, oxfendazole, parbendazole, flubendazole; febantel, netobimin, thiophanate; thiabendazole, cambendazole;
(b) salicylanilide-based anthelmintics: closantel, oxyclozanide, rafoxanide, niclosamide;
(c) substituted phenol-based anthelmintics: nitroxinil, nitroscanate;
(d) pyrimidine-based anthelmintics: pyrantel, morantel;
(e) imidazothiazole-based anthelmintics: levamisole, tetramisole;
(f) tetrahydropyrimidine-based anthelmintics: praziquantel, epsiprantel; and
(g) other anthelmintics: cyclodien, ryania, clorsulon, metronidazole, demiditraz; piperazine, diethylcarbamazine, dichlorophen, monepantel, tribendimidine, amidantel; thiacetarsamide, melorsamine, arsenamide.

Specific examples of the fungicides which can be mixed with or used in combination with the insecticide, acaricide or nematicide of the present invention are shown below.

(1) Nucleic acid biosynthesis inhibitors:
(a) RNA polymerase I inhibitors: benalaxyl, benalaxyl-M, furalaxyl, metalaxyl, metalaxyl-M; oxadixyl; clozylacon, ofurace;
(b) adenosine deaminase inhibitors: bupirimate, dimethirimol, ethirimol; (c) DNA/RNA synthesis inhibitors: hymexazol, octhilinone;
(d) DNA topoisomerase II inhibitors: oxolinic acid.

(2) Mitotic inhibitors and cell division inhibitors:
(a) β-tubulin polymerization inhibitors: benomyl, carbendazim, chlorfenazole, fuberidazole, thiabendazole; thiophanate, thiophanate methyl; diethofencarb; zoxamide; ethaboxam;
(b) cell division inhibitors: pencycuron;
(c) delocalization inhibitors of spectrin-like protein: fluopicolide.

(3) Respiration inhibitors:
(a) complex I NADH oxidoreductase inhibitors: diflumetorim; tolfenpyrad; (b) complex II succinate dehydrogenase inhibitors: benodanil, flutolanil, mepronil; isofetamid; fluopyram; fenfuram, furmecyclox; carboxin, oxycarboxin; thifluzamide; benzovindiflupyr, bixafen, fluxapyroxad, furametpyr, isopyrazam, penflufen, penthiopyrad, sedaxane; boscalid;
(c) complex III ubiquinol oxidase Qo inhibitors: azoxystrobin, coumoxystrobin, coumethoxystrobin, enoxastrobin, flufenoxystrobin, picoxystrobin, pyraoxystrobin; pyraclostrobin, pyrametostrobin, triclopyricarb; kresoximmethyl, trifloxystrobin; dimoxystrobin, fenaminstrobin, metominostrobin, orysastrobin; famoxadone; fluoxastrobin; fenamidone; pyribencarb;
(d) complex III ubiquinol reductase Qi inhibitors: cyazofamid; amisulbrom;

(e) oxidative phosphorylation uncouplers: binapacryl, meptyldinocap, dinocap; fluazinam; ferimzone;
(f) oxidative phosphorylation inhibitors (ATP synthase inhibitors): fentin acetate, fentin chloride, fentin hydroxide;
(g) ATP production inhibitor: silthiofam;
(h) complex III: Qx (unknown) inhibitor of cytochrome bcl (ubiquinone reductase): ametoctradin.

(4) Amino acid and protein synthesis inhibitors
(a) methionine biosynthesis inhibitors: andoprim, cyprodinil, mepanipyrim, pyrimethanil;
(b) protein synthesis inhibitors: blasticidin S; kasugamycin, kasugamycin hydrochloride; streptomycin; oxytetracycline.

(5) Signal transduction inhibitors:
(a) Signal transduction inhibitors: quinoxyfen, proquinazid;
(b) MAP/histidine kinase inhibitors in osmotic signal transduction: fenpiclonil, fludioxonil; chlozolinate, iprodione, procymidone, vinclozolin.

(6) Lipid and cell membrane synthesis inhibitors:
(a) phospholipid biosynthesis and methyltransferase inhibitors: edifenphos, iprobenfos, pyrazophos; isoprothiolane;
(b) lipid peroxidation agents: biphenyl, chloroneb, dicloran, quintozene, tecnazene, tolclofos-methyl; etridiazole;
(c) agents acting on cell membranes: iodocarb, propamocarb, propamocarb hydrochloride, propamocarb-fosetylate, prothiocarb;
(d) microorganisms disturbing pathogenic cell membranes: *Bacillus subtilis, Bacillus subtilis* strain QST713, *Bacillus subtilis* strain FZB24, *Bacillus subtilis* strain MBI600, *Bacillus subtilis* strain D747;
(e) agents disturbing cell membranes: extracts of *Melaleuca alternifolia* (tea tree).

(7) Sterol biosynthesis inhibitors of cell membranes:
(a) C14 position demethylation inhibitors in sterol biosynthesis: triforine; pyrifenox, pyrisoxazole; fenarimol, flurprimidol, nuarimol; imazalil, imazalil sulfate, oxpoconazole, pefurazoate, prochloraz, triflumizole, viniconazole; azaconazole, bitertanol, bromconazole, cyproconazole, diclobutrazol, difenoconazole, diniconazole, diniconazole-M, epoxiconazole, etaconazole, fenbuconazole, fluquinconazole, flusilazole, flutriafol, fluconazole, fluconazole-cis, hexaconazole, imibenconazole, ipconazole, metconazole, myclobutanil, penconazole, propiconazole, quinconazole, simeconazole, tebuconazole, tetraconazole, triadimefon, triadimenol, triticonazole; prothioconazole, voriconazole;
(b) inhibitors of Δ14 reductase and Δ8→Δ7-isomerase in sterol biosynthesis: aldimorph, dodemorph, dodemorph acetate, fenpropimorph, tridemorph; fenpropidine, piperalin; spiroxamine;
(c) 3-keto reductase inhibitors in C4 position demethylation in sterol biosynthesis system: fenhexamid; fenpyrazamine;
(d) squalene epoxidase inhibitors in sterol biosynthesis system: pyributicarb; naftifine, terbinafine.

(8) Cell wall synthesis inhibitors
(a) trehalase inhibitor: validamycin;
(b) chitin synthetase inhibitors: polyoxins, polyoxorim;
(c) cellulose synthetase inhibitors: dimethomorph, flumorph, pyrimorph; benthiavalicarb, iprovalicarb, tolprocarb, valifenalate; mandipropamid.

(9) Melanin biosynthesis inhibitors
(a) reductase inhibitors in melanin biosynthesis: fthalide; pyroquilon; tricyclazole;
(b) anhydrase inhibitors in melanin biosynthesis: carpropamid; diclocymet; fenoxanil;

(10) Resistance inducers of host plants:

(a) agents acting on salicylic acid synthetic pathway: acibenzolar-S-methyl;

(b) other agents: probenazole; tiadinil; isotianil; laminarin; extraction liquid of *Fallopia sachalinensis.*

(11) agents with unknown actions: cymoxanil, fosetyl-aluminium, phosphoric acid (phosphates), tecloftalam, triazoxide, flusulfamide, diclomezine, methasulfocarb, cyflufenamid, metrafenone, pyriofenone, dodine, dodine free base, flutianil.

(12) agents having multiple points of action: copper (copper salts), Bordeaux mixture, copper hydroxide, copper naphthalate, copper oxide, copper oxychloride, copper sulfate, sulfur, sulfur products, calcium polysulfide; ferbam, mancozeb, maneb, mancopper, metiram, polycarbamate, propineb, thiram, zineb, ziram; captan, captafol, folpet; chlorothalonil; dichlofluanid, tolylfluanid; guazatine, iminoctadine acetates (iminoctadine triacetate), iminoctadine albesilates (iminoctadine trialbesilate); anilazine; dithianon; chinomethionate; fluoroimide.

(13) Other agents: DBEDC, fluor folpet, guazatine acetate, bis (8-quinolinolato) copper (II), propamidine, chloropicrin, cyprofuram, agrobacterium, bethoxazin, diphenylamine, methyl isothiocyanate (MITC), mildiomycin, capsaicin, cufraneb, cyprosulfamide, dazomet, debacarb, dichlorophen, difenzoquat, difenzoquat methylsulfonate, flumetover, fosetyl calcium, fosetyl sodium, irumamycin, natamycin, nitrothal-isopropyl, oxamocarb, propanosine-sodium, pyrrolnitrin, tebufloquin, tolnifanide, zarilamid, algophase, amicarthiazol, oxathiapiprolin, metiram zinc, benthiazole, trichlamide, uniconazole, mildiomycin, oxyfenthiin, picarbutrazox.

Specific examples of the plant regulators which can be mixed with or used in combination with the insecticide, acaricide or nematicide of the present invention are shown below.

Abscisic acid, kinetin, benzylaminopurine, 1,3-diphenylurea, forchlorfenuron, thidiazuron, chlorphenuron, dihydroseatin, gibberellin A, gibberellin A4, gibberellin A7, gibberellin A3, 1-methylcyclopropane, N-acetyl aminoethoxyvinyl glycine (aka: abiglycine), aminooxyacetic acid, silver nitrate, cobalt chloride, IAA, 4-CPA, chloroprop, 2,4-D, MCPB, indole-3-butyric acid, dichlorprop, phenothiol, 1-naphthylacetamide, ethychlozate, croxyfonac, maleic hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl) amino butyric acid; ethephon, chlormequat, mepiquat chloride, benzyl adenine, 5-aminolevulinic acid.

The insecticidal or acaricidal agent of the present invention can effectively control drug-resistant strains of mites and ticks. For example, mites and ticks having resistance to the above-mentioned insecticides or acaricides can be effectively controlled. In particular, mites and ticks that are resistant to mitochondrial electron transport complex II inhibitors (such as cyenopyrafen and pyflubumide), acetyl CoA carboxylase inhibitors (such as spiromesifen) and chloride channel activators (such as milbemectin) can be effectively controlled.

[Endoparasite Control- or Extermination Agent]

The endoparasite control- or extermination agent of the present invention contains at least one selected from the phenoxyurea compounds of the present invention as an active ingredient.

The parasite to be targeted by the endoparasite control- or extermination agent of the present invention is parasitic in the bodies of host animals, especially warm blooded animals and fish (endoparasite). Examples of host animals for which the endoparasite control- or exterminating agent of the present invention is effective include warm-blooded animals such as humans, domestic mammals (for example, cattle, horses, pigs, sheep, goats and the like), laboratory animals (for example, mice, rats, gerbils and the like), pet animals (for example, hamsters, guinea pigs, dogs, cats, horses, squirrels, rabbits, ferrets, and the like), wild and zoo mammals (monkeys, foxes, deers, buffaloes and the like), domestic fowls (turkeys, ducks, chickens, quails, geese and the like) and pet birds (pigeons, parrots, hill mynas, Java sparrows, parakeets, society finches, canaries and the like); or fish such as salmon, trout and nishikigoi. By controlling and exterminating parasites, it is possible to prevent or treat parasitic diseases mediated by the parasites.

Examples of the parasites to be controlled or exterminated include the followings.

(1) Nematodes of the Order Dioctophymatida (a) kidney worms of the family Dioctophymatidae, for example, species belonging to the genus *Dioctophyma* (*Dioctophyma* spp.) such as *Dioctophyma renale*; and (b) kidney worms of the family Soboliphymatidae, for example, species belonging to the genus *Soboliphyme* (*Soboliphyme* spp.) such as *Soboliphyme abei* and *Soboliphyme baturini.*

(2) Nematodes of the Order Trichocephalida (a) trichina worms of the family Trichinellidae, for example, species belonging to the genus *Trichinella* (*Trichinella* spp.) such as *Trichinella spiralis*; and (b) whipworms of the family Trichuridae, for example, species belonging to the genus *Capillaria* (*Capillaria* spp.) such as *Capillaria annulata, Capillaria contorta, Capillaria hepatica, Capillaria perforans, Capillaria plica*, and *Capillaria suis*; and species belonging to the genus *Trichuris* (*Trichuris* spp.) such as *Trichuris vulpis, Trichuris discolor, Trichuris ovis, Trichuris skrjabini*, and *Trichuris suis.*

(3) Nematodes of the Order Rhabditida threadworms of the family Strongyloididae, for example, species belonging to the genus *Strongyloides* (*Strongyloides* spp.) such as *Strongyloides papillosus, Strongyloides planiceps, Strongyloides ransomi, Strongyloides suis, Strongyloides stercoralis, Strongyloides tumefaciens*, and *Strongyloides ratti.*

(4) Nematodes of the Order Strongylida hookworms of the family Ancylostomatidae, for example, species belonging to the genus *Ancylostoma* (*Ancylostoma* spp.) such as *Ancylostoma braziliense, Ancylostoma caninum, Ancylostoma duodenale*, and *Ancylostoma tubaeforme*; species belonging to the genus *Uncinaria* (*Uncinaria* spp.) such as *Uncinaria stenocephala*; and species belonging to the genus *Bunostomum* (*Bunostomum* spp.) such as *Bunostomum phlebotomum* and *Bunostomum trigonocephalum.*

(5) Nematodes of the Order Strongylida (a) nematodes of the family Angiostrongylidae, for example, species belonging to the genus *Aelurostrongylus* (*Aelurostrongylus* spp.) such as *Aelurostrongylus abstrusus*; and species belonging to the genus *Angiostrongylus* (*Angiostrongylus* spp.) such as *Angiostrongylus vasorum* and *Angiostrongylus cantonesis;*

(b) nematodes of the family Crenosomatidae, for example, species belonging to the genus *Crenosoma* (*Crenosoma* spp.) such as *Crenosoma aerophila* and *Crenosoma vulpis;*

(c) nematodes of the family Filaroididae, for example, species belonging to the genus *Filaroides* (*Filaroides* spp.) such as *Filaroides hirthi* and *Filaroides osleri;*

(d) lungworms of the family Metastrongylidae, for example, species belonging to the genus *Metastrongylus* (*Metastrongylus* spp.) such as *Metastrongylus apri, Metastrongylus asymmetricus, Metastrongylus pudendotectus* and *Metastrongylus salmi*; and (e) gapeworms of the family Syngamidae, for example, species belonging to the genus *Cyathostoma* (*Cyathostoma* spp.) such as *Cyathostoma bronchialis*; and species belonging to the genus *Syngamus* (*Syngamus* spp.) such as *Syngamus skrjabinomorpha* and *Syngamus trachea*.

(6) Nematodes of the Order Strongylida (a) nematodes of the family Molineidae, for example, species belonging to the genus *Nematodirus* (*Nematodirus* spp.) such as *Nematodirus filicollis* and *Nematodirus spathiger*;

(b) nematodes of the family Dictyocaulidae, for example, species belonging to the genus *Dictyocaulus* (*Dictyocaulus* spp.) such as *Dictyocaulus filaria* and *Dictyocaulus viviparus*;

(c) nematodes of the family Haemonchidae, for example, species belonging to the genus *Haemonchus* (*Haemonchus* spp.) such as *Haemonchus contortus*; and species belonging to the genus *Mecistocirrus* (*Mecistocirrus* spp.) such as *Mecistocirrus digitatus*;

(d) nematodes of the family Haemonchidae, for example, species belonging to the genus *Ostertagia* (*Ostertagia* spp.) such as *Ostertagia ostertagi*;

(e) nematodes of the family Heligmonellidae, for example, species belonging to the genus *Nippostrongylus* (*Nippostrongylus* spp.) such as *Nippostrongylus braziliensis*; and (f) nematodes of the family Trichostrongylidae, for example, species belonging to the genus *Trichostrongylus* (*Trichostrongylus* spp.) such as *Trichostrongylus axei, Trichostrongylus colubriformis* and *Trichostrongylus tenuis*; species belonging to the genus *Hyostrongylus* (*Hyostrongylus* spp.) such as *Hyostrongylus rubidus*; and species belonging to the genus *Obeliscoides* (*Obeliscoides* spp.) such as *Obeliscoides cuniculi*.

(7) Nematodes of the Order Strongylida (a) nematodes of the family Chabertiidae, for example, species belonging to the genus *Chabertia* (*Chabertia* spp.) such as *Chabertia ovina*; and species belonging to the genus *Oesophagostomum* (*Oesophagostomum* spp.) such as *Oesophagostomum brevicaudatum, Oesophagostomum columbianum, Oesophagostomum dentatum, Oesophagostomum georgianum, Oesophagostomum maplestonei, Oesophagostomum quadrispinulatum, Oesophagostomum radiatum, Oesophagostomum venulosum* and *Oesophagostomum watanabei*;

(b) nematodes of the family Stephanuridae, for example, species belonging to the genus *Stephanurus* (*Stephanurus* spp.) such as *Stephanurus dentatus*; and (c) nematodes of the family Strongylidae, for example, species belonging to the genus *Strongylus* (*Strongylus* spp.) such as *Strongylus asini, Strongylus edentatus, Strongylus equinus* and *Strongylus vulgaris*.

(8) Nematodes of the Order Oxyurida nematodes of the family Oxyuridae, for example, species belonging to the genus *Enterobius* (*Enterobius* spp.) such as *Enterobius anthropopitheci* and *Enterobius vermicularis*; species belonging to the genus *Oxyuris* (*Oxyuris* spp.) such as *Oxyuris equi*; and species belonging to the genus *Passalurus* (*Passalurus* spp.) such as *Passalurus ambiguus*.

(9) Nematodes of the Order Ascaridida (a) nematodes of the family Ascaridiidae, for example, species belonging to the genus *Ascaridia* (*Ascaridia* spp.) such as *Ascaridia galli*;

(b) nematodes of the family Heterakidae, for example, species belonging to the genus *Heterakis* (*Heterakis* spp.) such as *Heterakis beramporia, Heterakis brevispiculum, Heterakis gallinarum, Heterakis pusilla* and *Heterakis putaustralis*;

(c) nematodes of the family Anisakidae, for example, species belonging to the genus *Anisakis* (*Anisakis* spp.) such as *Anisakis simplex*;

(d) nematodes of the family Ascarididae, for example, species belonging to the genus *Ascaris* (*Ascaris* spp.) such as *Ascaris lumbricoides* and *Ascaris suum*; and species belonging to the genus *Parascaris* (*Parascaris* spp.) such as *Parascaris equorum*; and (e) nematodes of the family Toxocaridae, for example, species belonging to the genus *Toxocara* (*Toxocara* spp.) such as *Toxocara canis, Toxocara leonina, Toxocara suum, Toxocara vitulorum* and *Toxocara cati*.

(10) Nematodes of the Order Spirurida (a) nematodes of the family Onchocercidae, for example, species belonging to the genus *Brugia* (*Brugia* spp.) such as *Brugia malayi, Brugia pahangi* and *Brugia patei*; species belonging to the genus *Dipetalonema* (*Dipetalonema* spp.) such as *Dipetalonema reconditum*; species belonging to the genus *Dirofilaria* (*Dirofilaria* spp.) such as *Dirofilaria immitis*; species belonging to the genus *Filaria* (*Filaria* spp.) such as *Filaria oculi*; and species belonging to the genus *Onchocerca* (*Onchocerca* spp.) such as *Onchocerca cervicalis, Onchocerca gibsoni* and *Onchocerca gutturosa*;

(b) nematodes of the family Setariidae, for example, species belonging to the genus *Setaria* (*Setaria* spp.) such as *Setaria digitata, Setaria equina, Setaria labiatopapillosa* and *Setaria marshalli*; and species belonging to the genus *Wuchereria* (*Wuchereria* spp.) such as *Wuchereria bancrofti*; and (c) nematodes of the family Filariidae, for example, species belonging to the genus *Parafilaria* (*Parafilaria* spp.) such as *Parafilaria multipapillosa*; and species belonging to the genus *Stephanofilaria* (*Stephanofilaria* spp.) such as *Stephanofilaria assamensis, Stephanofilaria dedoesi, Stephanofilaria kaeli, Stephanofilaria okinawaensis* and *Stephanofilaria stilesi*.

(11) Nematodes of the Order Spirurida (a) nematodes of the family Gnathostomatidae, for example, species belonging to the genus *Gnathostoma* (*Gnathostoma* spp.) such as *Gnathostoma doloresi* and *Gnathostoma spinigerum*;

(b) nematodes of the family Habronematidae, for example, species belonging to the genus *Habronema* (*Habronema* spp.) such as *Habronema majus, Habronema microstoma* and *Habronema muscae*; and species belonging to the genus *Draschia* (*Draschia* spp.) such as *Draschia megastoma*;

(c) nematodes of the family Physalopteridae, for example, species belonging to the genus *Physaloptera* (*Physaloptera* spp.) such as *Physaloptera canis, Physaloptera cesticillata, Physaloptera erdocyona, Physaloptera felidis, Physaloptera gemina, Physaloptera papilloradiata, Physaloptera praeputialis, Physaloptera pseudopraerutialis, Physaloptera rara, Physaloptera sibirica* and *Physaloptera vulpineus*;

(d) nematodes of the family Gongylonematidae, for example, species belonging to the genus *Gongylonema* (*Gongylonema* spp.) such as *Gongylonema pulchrum*;

(e) nematodes of the family Spirocercidae, for example, species belonging to the genus *Ascarops* (*Ascarops* spp.) such as *Ascarops strongylina*; and (f) nematodes of the family Thelaziidae, for example, species belonging to the genus *Thelazia* (*Thelazia* spp.) such as *Thelazia callipaeda, Thelazia gulosa, Thelazia lacrymalis, Thelazia rhodesi* and *Thelazia skrjabini*.

[Ectoparasite Control Agent]

The ectoparasite control agent of the present invention contains at least one selected from the phenoxyurea compounds of the present invention as an active ingredient. The phenoxyurea compound of the present invention is excellent in the effect of controlling ectoparasites which harm humans and animals.

Examples of ectoparasites include mites and ticks, lice, fleas, mosquitoes, stable flies, flesh flies and the like.

Examples of host animals to be treated with the ectoparasite control agent of the present invention include warm-blooded animals including pet animals such as dogs and cats; pet birds; domestic animals such as cattle, horses, pigs and sheep; domestic fowls; and the like. In addition, honey bees, stag beetles and beetles can be exemplified.

The ectoparasites are parasitic in and on host animals, especially the warm-blooded animals. More specifically, the ectoparasites are parasitic in and on the back, armpit, lower abdomen, inner thigh and the like of the host animals and obtain nutritional sources such as blood and dandruff from the animals to live.

The ectoparasite control agent of the present invention can be applied by a known veterinary method (topical, oral, parenteral or subcutaneous administration). As a method therefor, a method of orally administering tablets, capsules, mixed feeds or the like to the animals; a method of administering to the animals by using an immersion liquid, suppository, injection (intramuscular, subcutaneous, intravenous, intraperitoneal or the like) or the like; a method of topically administering by spraying, pouring-on or spotting-on an oily or aqueous liquid preparation; a method of kneading an ectoparasite control agent in a resin, molding the kneaded product into an appropriate shape such as a collar, ear tag or the like, and attaching and topically administering the resultant to the animals; and the like can be mentioned.

Specific examples of the ectoparasites which can be controlled by the ectoparasite control agent of the present invention are shown below.

(1) Acari

Mites belonging to the family Dermanyssidae, mites belonging to the family Macronyssidae, mites belonging to the family Laelapidae, mites belonging to the family Varroidae, mites belonging to the family Argasidae, mites belonging to the family Ixodidae, mites belonging to the family Psoroptidae, mites belonging to the family Sarcoptidae, mites belonging to the family Knemidokoptidae, mites belonging to the family Demodixidae, mites belonging to the family Trombiculidae, insect-parasitic mites such as *Coleopterophagus berlesei* or the like.

(2) Phthiraptera

Lice belonging to the family Haematopinidae, lice belonging to the family Linognathidae, chewing lice belonging to the family Menoponidae, chewing lice belonging to the family Philopteridae, chewing lice belonging to the family Trichodectidae;

(3) Siphonaptera

Fleas of the family Pulicidae, for example, species belonging to the genus *Ctenocephalides* (*Ctenocephalides* spp.) such as *Ctenocephalides canis* and *Ctenocephalides felis*;

fleas belonging to the family Tungidae, fleas belonging to the family Ceratophyllidae, fleas belonging to the family Leptopsyllidae.

(4) Hemiptera (5) Insect pests of the order Diptera

Mosquitoes belonging to the family Culicidae, black flies belonging to the Simuliidae family, biting midges belonging to the family Ceratopogonidae, horseflies belonging to the family Tabanidae, flies belonging to the family Muscidae, tsetse flies belonging to the family Glossinidae; flesh flies belonging to the family Sarcophagidae, flies belonging to the family Hippoboscidae, flies belonging to the family Calliphoridae, flies belonging to the family Oestridae.

[Control Agents for Other Pests]

In addition, the ectoparasite control agent of the present invention is excellent in the effect of controlling insect pests having a stinger or venom which harm humans and animals, insect pests that mediate various pathogens/pathogenic microbes, and insect pests that cause discomfort to humans (such as toxic pests, hygiene pests and unpleasant pests).

Specific examples thereof are shown below.

(1) Insect Pests of the Order Hymenoptera

Bees belonging to the family Argidae, bees belonging to the family Cynipidae, bees belonging to the family Diprionidae, ants belonging to the family Formicidae, bees belonging to the family Mutillidae, bees belonging to the family Vespidae.

(2) Other Pests

Cockroaches (Blattodea), termites, spiders (Araneae), centipedes, millipedes, crustaceans, bedbugs (*Cimex lectularius*).

[Pharmaceutical Formulation]

Although some pharmaceutical formulations of the pest control agent, insecticide, acaricide, nematicide, endoparasite control- or extermination agent and ectoparasite control agent of the present invention are shown, additives and the addition ratios should not be limited to these examples and can be modified over a wide range. The term "part" in the formulations indicates "part by weight".

The formulations for agricultural and horticultural use and for paddy rice are shown below.

(Formulation 1: Wettable Powder)

40 parts of the phenoxyurea compound of the present invention, 53 parts of diatomaceous earth, 4 parts of a higher alcohol sulfuric acid ester and 3 parts of an alkyl naphthalene sulfonate are uniformly mixed and finely pulverized to obtain a wettable powder containing 40% of an active ingredient.

(Formulation 2: Emulsion)

30 parts of the phenoxyurea compound of the present invention, 33 parts of xylene, 30 parts of dimethylformamide and 7 parts of a polyoxyethylene alkyl allyl ether are mixed and dissolved to obtain an emulsion containing 30% of an active ingredient.

(Formulation 3: Granule)

5 parts of the phenoxyurea compound of the present invention, 40 parts of talc, 38 parts of clay, 10 parts of bentonite and 7 parts of a sodium alkylsulfate are uniformly mixed and finely pulverized, and then granulated into a granular form having a diameter of 0.5 to 1.0 mm to obtain a granule containing 5% of an active ingredient.

(Formulation 4: Granule)

5 parts of the phenoxyurea compound of the present invention, 73 parts of clay, 20 parts of bentonite, 1 part of sodium dioctyl sulfosuccinate and 1 part of potassium phosphate are thoroughly pulverized and mixed, and water is added and thoroughly kneaded, followed by granulation and drying to obtain a granule containing 5% of an active ingredient.

(Formulation 5: Suspension)

10 parts of the phenoxyurea compound of the present invention, 4 parts of a polyoxyethylene alkyl allyl ether, 2 parts of a polycarboxylic acid sodium salt, 10 parts of glycerin, 0.2 parts of xanthan gum and 73.8 parts of water are mixed and subjected to wet grinding until the particle size becomes 3 microns or less to obtain a suspension containing 10% of an active ingredient.

The formulations of an endoparasite control- or extermination agent or an ectoparasite control agent are shown below.

(Formulation 6: Granule)

5 parts of the phenoxyurea compound of the present invention are dissolved in an organic solvent to obtain a solution, the solution is sprayed onto 94 parts of kaolin and 1 part of white carbon, and then the solvent is evaporated under reduced pressure. This type of granule can be mixed with animal feed.

(Formulation 7: Injection)

0.1 to 1 part of the phenoxyurea compound of the present invention and 99 to 99.9 parts of peanut oil are uniformly mixed and then sterilized by filtration through a sterilizing filter.

(Formulation 8: Pour-on Agent)

5 parts of the phenoxyurea compound of the present invention, 10 parts of a myristic acid ester and 85 parts of isopropanol are uniformly mixed to obtain a pour-on agent.

(Formulation 9: Spot-on Agent)

10 to 15 parts of the phenoxyurea compound of the present invention, 10 parts of a palmitic acid ester and 75 to 80 parts of isopropanol are uniformly mixed to obtain a spot-on agent.

(Formulation 10: Spraying Agent)

1 part of the phenoxyurea compound of the present invention, 10 parts of propylene glycol and 89 parts of isopropanol are uniformly mixed to obtain a spraying agent.

Next, the present invention will be described in more detail by showing examples. However, the present invention is in no way limited by the following examples.

EXAMPLE 1

Production of 2-{3-[3-Bromo-5-(trifluoromethyl)phenoxy]-3-ethylureido}-2-methyl-N-(2,2,2-trifluoroethyl)propanamide (Compound No. 1-1)

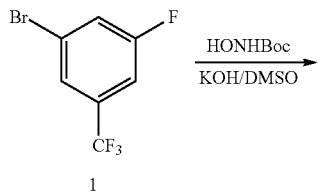

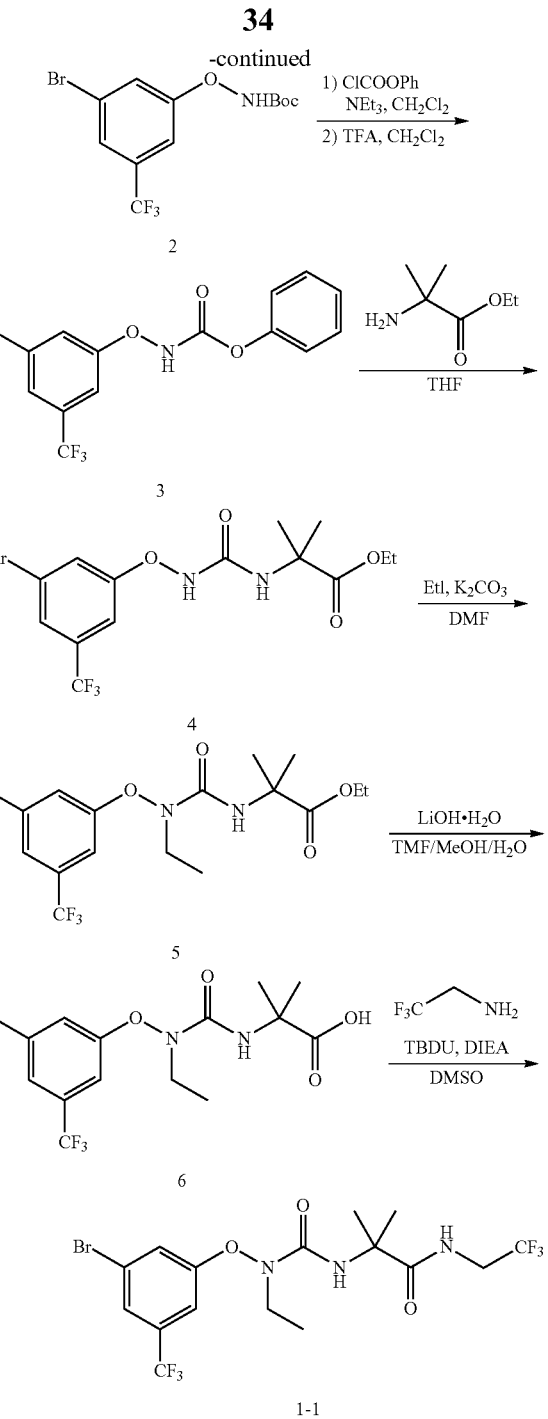

(Step 1) Synthesis of tert-Butyl N-[3-bromo-5-(trifluoromethyl)phenoxy]carbamate (Compound 2)

1-Bromo-3-fluoro-5-(trifluoromethyl) benzene (50.0 g) and Boc-hydroxylamine (32.9 g) were dissolved in DMSO (40 ml), potassium hydroxide (32.6 g) was added thereto, and the resulting mixture was stirred for 5 hours at room temperature. After completion of the reaction, aqueous ammonium chloride was added thereto and the resulting mixture was extracted with diethyl ether. Magnesium sulfate was added to the obtained organic layer, and after drying and filtration, the solvent was distilled off under reduced pressure to obtain a compound 2 (75.6 g).

$^1$H-NMR (CDCl$_3$/TMS, δ (ppm)) 7.58 (s, 1H), 7.47 to 7.46 (m, 1H), 7.43 (s, 1H), 7.30 (s, 1H), 1.51 (s, 9H).

(Step 2) Synthesis of Phenyl N-[3-bromo-5-(trifluoromethyl)phenoxy]carbamate (Compound 3)

The compound 2 (75.6 g) was dissolved in 824 ml of dichloromethane, triethylamine (31.3 g) was added under ice cooling, phenyl chloroformate (36.3 g) was added dropwise, and the resulting mixture was stirred for 2 hours under ice cooling. After completion of the reaction, aqueous ammonium chloride was added and the dichloromethane layer was separated, magnesium sulfate was added to the resultant, and after drying and filtration, the solvent was distilled off under reduced pressure.

160 ml of dichloromethane was added to the obtained residue, 79 ml of trifluoroacetic acid was added dropwise under ice cooling, and the resulting mixture was stirred at room temperature for 4 hours. The reaction solution was neutralized with a saturated aqueous sodium bicarbonate solution and then extracted with ethyl acetate. Magnesium sulfate was added to the obtained organic layer, and after drying and filtration, the solvent was distilled off under reduced pressure. The precipitated crystals were washed with hexane to obtain a compound 3 (73.0 g, 3 step yield: 94%).

$^1$H-NMR (CDCl$_3$/TMS, δ (ppm)) 8.08 (s, 1H), 7.55 to 7.54 (m, 1H), 7.48 (s, 1H), 7.42 to 7.38 (m, 3H), 7.29 to 7.25 (m, 1H), 7.20 to 7.18 (m, 2H).

(Step 3) Synthesis of Ethyl 2-{3-[3-bromo-5-(trifluoromethyl)phenoxy]ureido}-2-methylpropanoate (Compound 4)

Ethyl 2-amino-2-methylpropionate (6.10 g) was added to a THF solution (100 ml) of the compound 3 (16.9 g), and the resulting mixture was stirred at 60° C. for 7 hours. After completion of the reaction, the solvent was distilled off under reduced pressure, and the obtained residue was purified by silica gel column chromatography to obtain a compound 4 (11.9 g, yield: 64%).

$^1$H-NMR (CDCl$_3$/TMS, δ (ppm)) 7.95 (s, 1H), 7.58 (s, 1H), 7.48 (s, 1H), 7.40 (s, 1H), 6.33 (s, 1H), 4.21 (q, 2H), 1.61 (s, 6H), 1.27 (t, 3H).

(Step 4) Synthesis of Ethyl 2-{3-[3-bromo-5-(trifluoromethyl)phenoxy]-3-ethylureido}-2-methylpropanoate (Compound 5)

The compound 4 (11.9 g) was dissolved in DMF (92 ml), potassium carbonate (9.56 g) and iodoethane (4.49 g) were added, and the resulting mixture was stirred for 5 hours under ice cooling. After completion of the reaction, aqueous ammonium chloride was added thereto and the resulting mixture was extracted with ethyl acetate. The organic layer was dried over magnesium sulfate and filtered, and then the solvent was distilled off under reduced pressure. The obtained residue was purified by silica gel column chromatography to obtain a target compound 5 (10.8 g, yield: 85%).

$^1$H-NMR (CDCl$_3$/TMS, δ (ppm)) 7.54 (s, 1H), 7.48 (s, 1H), 7.36 (s, 1H), 6.24 (s, 1H), 4.20 (q, 2H), 3.66 (d, 2H), 1.57 (s, 6H), 1.28 (t, 3H), 1.17 (t, 3H).

(Step 5) Synthesis of 2-{3-[3-Bromo-5-(trifluoromethyl)phenoxy]-3-ethylureido}-2-methylpropanoic acid (Compound 6)

Lithium hydroxide monohydrate (1.93 g) was added to a THF/methanol/water (85 ml/21 ml/21 ml) solution of the compound 5 (15.6 g), and the resulting mixture was stirred for 10 hours. After completion of the reaction, 7% HCl (24.0 g) was added thereto and the resulting mixture was extracted with ethyl acetate. Magnesium sulfate was added to the obtained organic layer, and after drying and filtration, the solvent was distilled off under reduced pressure. The precipitated crystals were washed with hexane to obtain a compound 6 (13.6 g, yield: 93%).

$^1$H-NMR (CDCl$_3$/TMS, δ (ppm)) 7.54 to 7.53 (m, 1H), 7.50 (s, 1H), 7.36 (dd, 1H), 6.05 (s, 1H), 3.67 (q, 2H), 1.60 (s, 6H), 1.17 (t, 3H).

(Step 6) Synthesis of 2-{3-[3-Bromo-5-(trifluoromethyl)phenoxy]-3-ethylureido}-2-methyl-N-(2,2,2-trifluoroethyl)propanamide (Compound 1-1)

Diisopropylethylamine (0.88 g), trifluoroethylamine (0.26 g) and TBTU (0.87 g) were added to a DMSO (8 ml) solution of the compound 6 (0.70 g), and the resulting mixture was stirred overnight at room temperature. After completion of the reaction, aqueous ammonium chloride was added thereto and the resulting mixture was extracted with ethyl acetate. The organic layer was dried over magnesium sulfate and filtered, and then the solvent was distilled off under reduced pressure. The obtained residue was purified by silica gel column chromatography to obtain a target compound 1-1 (0.83 g, yield: 99%).

$^1$H-NMR (CDCl$_3$/TMS, δ (ppm)) 7.51 (s, 2H), 7.33 (s, 1H), 7.12 (t, 1H), 5.99 (s, 1H), 3.94 (dq, 2H), 3.67 (q, 2H), 1.57 (s, 6H), 1.17 (t, 3H).

EXAMPLE 2

Production of 2-{3-[3-Bromo-5-(trifluoromethyl)phenoxy]-3-ethylureido}-2-methyl-N-(2,2,2-trifluoroethyl)propanamide (Compound No. 1-1)

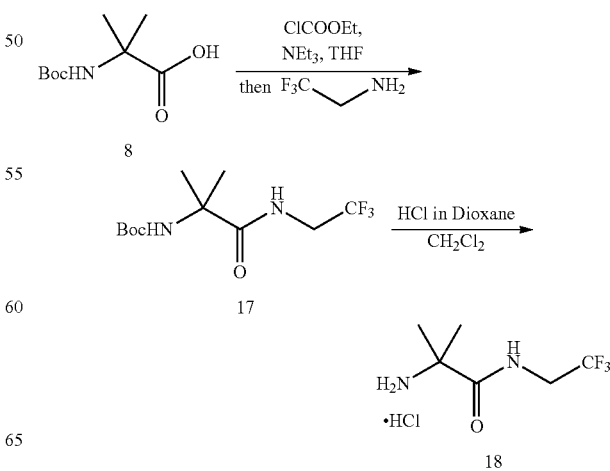

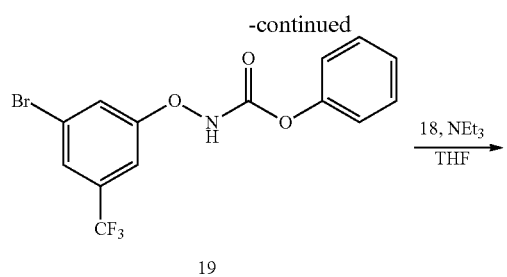

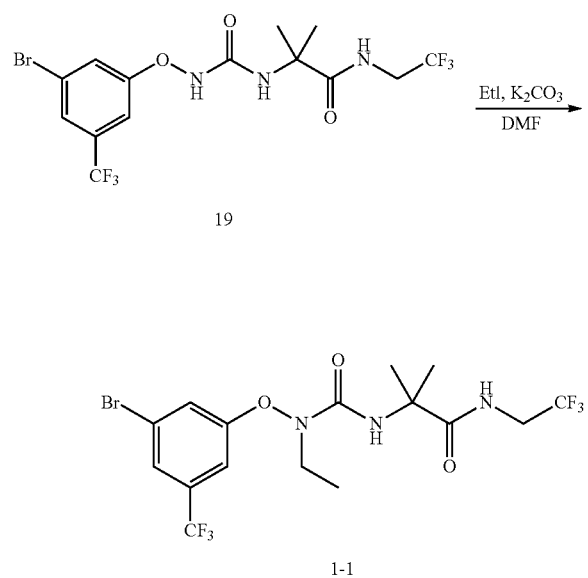

(Step 1) Synthesis of tert-Butyl N-[2-methyl-1-oxo-1-(2,2,2-trifluoroethylamino)propan-2-yl]carbamate (Compound 17)

2-(tert-Butoxycarbonylamino)-2-methylpropanoic acid (81.3 g) was dissolved in 1,000 ml of THF, triethylamine (40.5 g) was added, ethyl chloroformate (40.4 g) was added dropwise at −5° C., and then the resulting mixture was stirred for 20 minutes. Thereafter, trifluoroethylamine (59.4 g) was added at −5° C., and the resulting mixture was stirred at room temperature for 3 hours. After completion of the reaction, the reaction solution was poured into ice water and extracted with ethyl acetate. The organic layer was washed with an aqueous sodium bicarbonate solution and saturated brine in this order, and then magnesium sulfate was added thereto, and after drying and filtration, the solvent was distilled off under reduced pressure. The precipitated crystals were washed with hexane to obtain a compound 17 (94.7 g, yield: 83%).

(Step 2) Synthesis of 2-Amino-2-methyl-N-(2,2,2-trifluoroethyl)propanamide (Compound 18)

The compound 17 (94.6 g) was dissolved in 1,000 ml of dichloromethane, a 4 M hydrogen chloride solution in dioxane (480 ml) was added at 10° C., and the resulting mixture was stirred overnight at room temperature. After completion of the reaction, the solvent was distilled off under reduced pressure to obtain a compound 18 (70.4 g, yield: 96%).

(Step 3) Synthesis of 2-{3-[3-Bromo-5-(trifluoromethyl)phenoxy]ureido}-2-methyl-N-(2,2,2-trifluoroethyl)propanamide (Compound 19)

The compound 3 (30.0 g) was dissolved in THF (264 ml), the compound 18 (22.9 g) and triethylamine (18.8 g) were added thereto, and the resulting mixture was stirred under heating reflux for 4 hours. After completion of the reaction, the reaction solution was diluted by adding ethyl acetate, and washed with a 3N aqueous sodium hydroxide solution, aqueous ammonium chloride solution and saturated brine in this order. Then magnesium sulfate was added to the organic layer, and after drying and filtration, the solvent was distilled off under reduced pressure. The precipitated crystals were washed with diisopropyl ether to obtain a compound 19 (29.9 g, yield: 80%).

$^1$H-NMR (CDCl$_3$/TMS, δ (ppm)) 7.77 (s, 1H), 7.56 to 7.55 (m, 1H), 7.50 (s, 1H), 7.39 (s, 1H), 6.82 (t, 1H), 6.11 (s, 1H), 3.94 (dq, 2H), 1.62 (s, 6H).

(Step 4) Synthesis of 2-{3-[3-Bromo-5-(trifluoromethyl)phenoxy]-3-ethylureido}-2-methyl-N-(2,2,2-trifluoroethyl)propanamide (Compound 1-1)

The compound 19 (29.8 g) was dissolved in DMF (214 ml), potassium carbonate (10.6 g) and iodoethane (10.1 g) were added thereto under ice cooling, and the resulting mixture was stirred at room temperature for 5 hours. After completion of the reaction, aqueous ammonium chloride was added thereto and the resulting mixture was extracted with ethyl acetate. The organic layer was washed three times with saturated brine, then magnesium sulfate was added thereto, and after drying and filtration, the solvent was distilled off under reduced pressure. The obtained residue was purified by silica gel column chromatography to obtain a target compound 1-1 (29.5 g, yield: 93%).

$^1$H-NMR (CDCl$_3$/TMS, δ (ppm)) 7.51 (s, 2H), 7.33 (s, 1H), 7.12 (t, 1H), 5.99 (s, 1H), 3.94 (dq, 2H), 3.67 (q, 2H), 1.57 (s, 6H), 1.17 (t, 3H).

Some of the compounds of the present invention produced by the same method as in the above examples are shown in Tables 1 to 4. Table 2 shows substituents of the compound of formula (I-1). Table 3 shows substituents of the compound of formula (I-2). Table 4 shows substituents of the compound of formula (I-3). In the tables, properties, melting point (m.p.) or refractive index (nD) are shown together as physical properties of each compound.

It should be noted that in the tables, Me represents a methyl group, Et represents an ethyl group, $^n$Pr represents a normal propyl group, $^i$Pr represents an isopropyl group, $^c$Pr represents a cyclopropyl group, Bu represents an isobutyl group, $^t$Bu represents a tertiary butyl group, and $^c$Bu represents a cyclobutyl group, respectively.

TABLE 1

| Compound No. | Structure | Physical property |
|---|---|---|
| 1-2 | 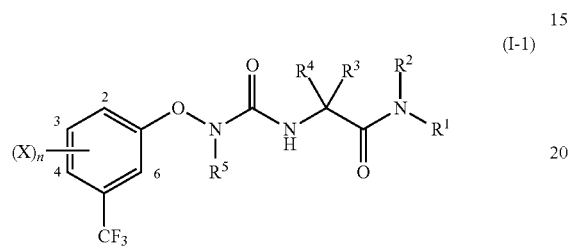 | m.p. 119-120° C. |

<br>

(I-1)

$$\text{(X)}_n \underset{4}{\overset{3}{\underset{\phantom{CF_3}}{\bigcirc}}}{}^{2}_{6}\text{—O—N(R}^5\text{)—C(=O)—NH—C(R}^3\text{)(R}^4\text{)—C(=O)—N(R}^1\text{)(R}^2\text{)}$$

TABLE 2

| Compound No. | R¹ | R² | R³ | R⁴ | R⁵ | (X)ₙ | Physical property |
|---|---|---|---|---|---|---|---|
| 2-1 | $^c$Pr | H | Me | Me | Et | 3-Br | m.p. 120-121° C. |
| 2-2 | —CH₂CN | H | Me | Me | Et | 3-Br | m.p. 121-122° C. |
| 2-3 | —CH₂$^c$Pr | H | Me | Me | Et | 3-Br | m.p. 73-74° C. |
| 2-4 | —CH₂CF₂CF₃ | H | Me | Me | Et | 3-Br | m.p. 70-71° C. |
| 2-5 | —CH₂CH₂CF₃ | H | Me | Me | Et | 3-Br | m.p. 81-83° C. |
| 2-6 | $^n$Pr | H | Me | Me | Et | 3-Br | m.p. 72-73° C. |
| 2-7 | $^i$Bu | H | Me | Me | Et | 3-Br | m.p. 88-90° C. |
| 2-8 | 1-CN-$^c$Pr | H | Me | Me | Et | 3-Br | m.p. 118-120° C. |
| 2-9 | 3,3-F₂-$^c$Bu | H | Me | Me | Et | 3-Br | m.p. 127-128° C. |
| 2-10 | H | H | Me | Me | Et | 3-Br | m.p. 130-131° C. |
| 2-11 | —CH₂CF₃ | H | Me | Me | Et | 4-Br | m.p. 90-92° C. |
| 2-12 | $^i$Pr | H | Me | Me | Et | 4-Br | m.p. 70-72° C. |
| 2-13 | $^c$Pr | H | Me | Me | Et | 4-Br | m.p. 96-98° C. |
| 2-14 | —CH₂CN | H | Me | Me | Et | 4-Br | amorphous |
| 2-15 | —CH₂—CH₂—CH₂— | | Me | Me | Et | 3-Br | m.p. 118-119° C. |
| 2-16 | —CH₂COOEt | H | Me | Me | Et | 3-Br | viscous oil |
| 2-17 | —CH₂CONHCH₂CF₃ | H | Me | Me | Et | 3-Br | m.p. 168-170° C. |
| 2-18 | —CH₂CF₃ | H | Me | Me | Et | 4-Cl | m.p. 92-94° C. |
| 2-19 | $^i$Pr | H | Me | Me | Et | 4-Cl | m.p. 77-78° C. |
| 2-20 | $^i$Pr | H | Me | Me | Et | 3-F₃ | m.p. 62-64° C. |
| 2-21 | —CH₂CF | H | Me | Me | Et | 3-CF₃ | m.p. 120-121° C. |
| 2-22 | —CH₂CN | H | Me | Me | Et | 3-CF₃ | m.p. 134-135° C. |
| 2-23 | $^c$Pr | H | Me | Me | Et | 3-CF₃ | m.p. 90-92° C. |
| 2-24 | —CH₂CHF₂ | H | Me | Me | Et | 3-F₃ | m.p. 87-88° C. |
| 2-25 | —CH₂CF₂CF₃ | H | Me | Me | Et | 3-Cl | m.p. 70-71° C. |
| 2-26 | —CH₂$^c$Pr | H | Me | Me | Et | 3-Cl | m.p. 83-85° C. |
| 2-27 | $^i$Pr | H | Me | Me | Et | 3-Cl | m.p. 78-84° C. |
| 2-28 | —CH₂CN | H | Me | Me | Et | 3-Cl | $n_D$ ( 20.3° C.) 1.4956 |
| 2-29 | —CH₂CF₃ | H | Me | Me | Et | 3-Cl | m.p. 99-100° C. |
| 2-30 | $^c$Pr | H | Me | Me | Et | 3-Cl | m.p. 129-130° C. |
| 2-31 | —CH₂CHF₂ | H | Me | Me | Et | 3-Cl | m.p. 78-79° C. |
| 2-32 | $^n$Pr | H | Me | Me | Et | 3-Cl | m.p. 90-93° C. |
| 2-33 | —CH₂CH₂SMe | H | Me | Me | Et | 3-Cl | $n_D$ ( 20.3° C.) 1.5092 |
| 2-34 | —CH₂CH₂CF₃ | H | Me | Me | Et | 3-Cl | $n_D$ ( 20.7° C.) 1.4701 |
| 2-35 | $^i$Pr | H | Me | Me | —CH₂C≡CH | 3-Br | m.p. 129-131° C. |
| 2-36 | iPr | H | Me | Me | Me | 3-Br | m.p. 96-98° C. |
| 2-37 | —CH₂CF₃ | H | Me | Me | Me | 3-Br | m.p. 99-100° C. |
| 2-38 | $^i$Pr | H | Me | Me | $^n$Pr | 3-Br | m.p. 130-131° C. |
| 2-39 | —CH₂CF₃ | H | Me | Me | $^n$Pr | 3-Br | m.p. 94-95° C. |
| 2-40 | $^i$Pr | H | Me | Me | —CH₂$^c$Pr | 3-Br | m.p. 124-124° C. |
| 2-41 | —CH₂CF₃ | H | Me | Me | —CH₂$^c$Pr | 3-Br | m.p. 114-115° C. |
| 2-42 | —CH₂CF₃ | H | Me | Me | —CH₂C≡CH | 3-Br | m.p. 119-120° C. |
| 2-43 | $^i$Pr | H | Me | Me | —CH₂CF₃ | 3-Br | m.p. 120-121° C. |
| 2-44 | —CH₂CF₃ | H | Me | Me | —CH₂CF₃ | 3-Br | m.p. 112-114° C. |
| 2-45 | $^i$Pr | H | Me | Me | —CH₂CHF₂ | 3-Br | m.p. 110-111° C. |

TABLE 2-continued

| Compound No. | R¹ | R² | R³ | R⁴ | R⁵ | $(X)_n$ | Physical property |
|---|---|---|---|---|---|---|---|
| 2-46 | —CH$_2$CF$_3$ | H | Me | Me | —CH$_2$CHF$_2$ | 3-Br | m.p. 97-99° C. |
| 2-47 | —CH$_2$CF$_3$ | H | $^i$Pr | H | Et | 3-Br | m.p. 151-152° C. |
| 2-48 | —CH$_2$CHF$_2$ | H | Me | Me | Et | 3-Br | m.p. 92-94° C. |
| 2-49 | —CH$_2$C≡CH | H | Me | Me | Et | 3-Br | m.p. 92-94° C. |
| 2-50 | —CH$_2$CH=CH$_2$ | H | Me | Me | Et | 3-Br | m.p. 68-70° C. |
| 2-51 | $^t$Bu | H | Me | Me | Et | 3-Br | m.p. 143-144° C. |
| 2-52 | $^c$Bu | H | Me | Me | Et | 3-Br | m.p. 113-115° C. |
| 2-53 | $^i$Pr | H | $^i$Pr | H | Et | 3-Br | m.p. 141-142° C. |
| 2-54 | $^c$Pr | H | $^i$Pr | H | Et | 3-Br | m.p. 116-117° C. |
| 2-55 | —CH$_2$CN | H | $^i$Pr | H | Et | 3-Br | m.p. 121-122° C. |
| 2-56 | —CH$_2$CHF$_2$ | H | $^i$Pr | H | Et | 3-Br | m.p. 123-124° C. |
| 2-57 | —CH$_2$$^c$Pr | H | $^i$Pr | H | Et | 3-Br | m.p. 119-120° C. |
| 2-58 | —CH$_2$CClF$_2$ | H | Me | Me | Et | 3-Br | m.p. 78-80° C. |
| 2-59 | 2-F—phenyl | H | Me | Me | Et | 3-Br | m.p. 119-120° C. |
| 2-60 | 2-CF$_3$—phenyl | H | Me | Me | Et | 3-Br | m.p. 124-125° C. |
| 2-61 | —CH$_2$CF$_3$ | H | Me | Me | Et | 3-Br | m.p. 131-133° C. |
| 2-62 | —CH$_2$CF$_3$ | Me | Me | Me | Et | 3-Br | m.p. 150-152° C. |
| 2-63 | —CH$_2$CF$_3$ | H | Me | Me | Et | 3-I | m.p. 136-137° C. |
| 2-64 | $^i$Pr | H | Me | Me | Et | 3-I | amorphous |

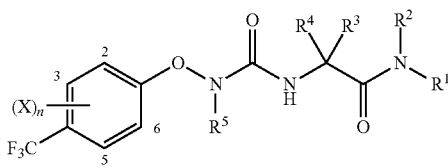

(I-2)

TABLE 3

| Compound No. | R¹ | R² | R³ | R⁴ | R⁵ | $(X)_n$ | Physical property |
|---|---|---|---|---|---|---|---|
| 3-1 | —CH$_2$CF$_3$ | H | Me | Me | Et | 3-Br | m.p. 98-99° C. |
| 3-2 | $^i$Pr | H | Me | Me | Et | 3-Br | viscous oil |
| 3-3 | $^c$Pr | H | Me | Me | Et | 3-Br | amorphous |
| 3-4 | —CH$_2$CN | H | Me | Me | Et | 3-Br | amorphous |
| 3-5 | $^n$Pr | H | Me | Me | Et | 3-Br | viscous oil |
| 3-6 | —CH$_2$CH$_2$CF$_3$ | H | Me | Me | Et | 3-Br | viscous oil |
| 3-7 | —CH$_2$CF$_3$ | H | Me | Me | Et | 3-Cl | m.p. 95-96° C. |
| 3-8 | $^i$Pr | H | Me | Me | Et | 3-Cl | m.p. 80-82° C. |
| 3-9 | $^c$Pr | H | Me | Me | Et | 3-Cl | amorphous |
| 3-10 | —CH$_2$CN | H | Me | Me | Et | 3-Cl | amorphous |
| 3-11 | —CH$_2$$^c$Pr | H | Me | Me | Et | 3-Br | viscous oil |
| 3-12 | —CH$_2$CF$_2$CF$_3$ | H | Me | Me | Et | 3-Cl | m.p. 92-94° C. |
| 3-13 | —CH$_2$$^c$Pr | H | Me | Me | Et | 3-Cl | m.p. 88-90° C. |

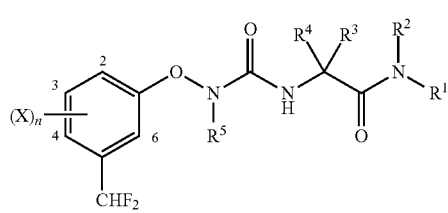

(I-3)

TABLE 4

| Compound No. | R¹ | R² | R³ | R⁴ | R⁵ | $(X)_n$ | Physical property |
|---|---|---|---|---|---|---|---|
| 4-1 | —CH$_2$CF$_3$ | H | Me | Me | Et | 3-Br | m.p. 111-113° C. |
| 4-2 | $^i$Pr | H | Me | Me | Et | 3-Br | m.p. 113-114° C. |
| 4-3 | —CH$_2$CHF$_2$ | H | Me | Me | Et | 3-Br | m.p. 84-85° C. |
| 4-4 | $^c$Pr | H | Me | Me | Et | 3-Br | m.p. 108-111° C. |
| 4-5 | —CH$_2$CN | H | Me | Me | Et | 3-Br | m.p. 138-140° C. |

Among the compounds shown in Tables 1 to 4, $^1$H-NMR (CDCl$_3$) was measured for compounds having physical properties of viscous oil or amorphous. Table 5 shows the measured values.

TABLE 5

| Compound No. | $^1$H-NMR (CDCl$_3$-d$_6$, δppm) |
|---|---|
| 2-14 | 7.69 (d, 1H), 7.46 (d, 1H), 7.44 (t, 1H), 7.21 (dd, 1H), 5.97 (s, 1H), 4.19 (d, 2H), 3.66 (q, 2H), 1.55 (s, 6H), 1.17 (t, 3H) |
| 2-16 | 7.54-7.53 (m, 1H), 7.49 (s, 1H), 7.36 (s, 1H), 6.73 (t, 1H), 6.29 (s, 2H), 4.03 (d, 2H), 3.67 (q, 2H), 1.60 (s, 6H), 1.29 (t, 3H), 1.17 (t, 3H) |
| 2-64 | 7.70 (s, 1H), 7.66 (s, 1H), 7.37 (s, 1H), 6.52 (s, 1H), 5.92 (d, 1H), 4.10-4.00 (m, 1H), 3.65 (d, 2H), 1.57 (s, 6H), 1.18-1.14 (m, 9H) |
| 3-2 | 7.65 (d, 1H), 7.53 (d, 1H), 7.18 (dd, 1H), 6.54 (s, 1H), 5.87 (d, 1H), 4.08-4.00 (m, 1H), 3.66 (br, 2H), 1.56 (s, 6H), 1.18-1.15 (m, 9H) |
| 3-3 | 7.66 (d, 1H), 7.52 (d, 1H), 7.18 (dd, 1H), 6.47 (s, 1H), 6.26 (s, 1H), 3.66(d, 2H), 2.73-2.67 (m, 1H), 1.54 (s, 6H), 1.16 (t, 3H), 0.86-0.73 (m, 2H), 0.55-0.43 (m, 2H) |
| 3-4 | 7.69 (d, 1H), 7.51 (d, 1H), 7.41 (t, 1H), 7.17 (dd, 1H), 5.87 (s, 1H), 4.19 (d, 2H), 3.68 (q, 2H), 1.55 (s, 6H), 1.18 (t, 3H) |
| 3-5 | 7.66 (d, 1H), 7.53 (d, 1H), 7.18 (dd, 1H), 6.49 (s, 1H), 6.16 (t, 1H), 3.67 (d, 2H), 3.23 (q, 2H), 1.58 (s, 6H), 1.57-1.49 (m, 2H), 1.17 (t, 3H), 0.92 (t, 3H) |
| 3-6 | 7.67 (d, 1H), 7.52 (d, 1H), 7.18 (dd, 1H), 6.61 (t, 1H), 6.13 (s, 1H), 3.67 (q, 2H), 3.54 (q, 2H), 2.42-2.30 (m, 2H), 1.54 (s, 6H), 1.16 (t, 3H) |
| 3-9 | 7.66 (d, 1H), 7.33 (d, 1H), 7.14 (dd, 1H), 6.52 (s, 1H), 6.33 (s, 1H), 3.66 (d, 2H), 2.73-2.67 (m, 1H), 1.55 (s, 6H), 1.16 (t, 3H), 0.85-0.72 (m, 2H), 0.55-0.44 (m, 2H) |
| 3-10 | 7.69 (d, 1H), 7.41 (t, 1H), 7.32 (d, 1H), 7.13 (dd, 1H), 5.97 (s, 1H), 4.19 (d, 2H), 3.68 (q, 2H), 1.55 (s, 6H), 1.18 (t, 3H) |

TABLE 5-continued

| Compound No. | $^1$H-NMR (CDCl$_3$-d$_6$, δppm) |
|---|---|
| 3-11 | 7.66 (d, 1H), 7.53 (d, 1H), 7.19 (dd, 1H), 6.50 (s, 1H), 6.18 (s, 1H), 3.67 (d, 2H), 3.13 (dd, 2H), 1.59 (s, 6H), 1.17 (t, 3H), 1.01-0.90 (m, 1H), 0.57-0.45 (m, 2H), 0.26-0.15 (m, 2H) |

[Biological Test]

The following test examples show that the compounds of the present invention are useful as an active ingredient of an insecticide, an acaricide or an ectoparasite control agent.

(Preparation of Test Emulsion)

5 parts by weight of the compound of the present invention, 93.6 parts by weight of dimethylformamide and 1.4 parts by weight of polyoxyethylene alkylaryl ether were mixed and dissolved to prepare an emulsion (I) containing 5% of an active ingredient.

The insecticidal rate was calculated by the following equation.

Insecticidal rate (%)=(number of dead insects/number of tested insects)×100

(Test Example 1) Efficacy Test Against *Tetranychus kanzawai*

Kidney bean plants were raised in No. 3 pots, and 8 adult females of *Tetranychus kanzawai* from Okayama Prefecture were inoculated on primary leaves. Then, the emulsion (I) was diluted with water so that the concentration of the compound was 125 ppm to obtain a chemical. This chemical was sprayed on the kidney bean plants. The kidney bean plants were placed in a thermostatic chamber at a temperature of 25° C. and a humidity of 65%. The life and death of *Tetranychus kanzawai* were investigated when 10 days had passed after the chemical spraying.

The compounds with numbers shown in Table 6 were tested for efficacy against *Tetranychus kanzawai*. All compounds showed an insecticidal rate of 90% or more against *Tetranychus kanzawai*.

TABLE 6

| 1-1 | 2-8 | 2-17 | 2-26 | 2-35 | 2-49 | 3-5 | 4-2 |
| 1-2 | 2-9 | 2-18 | 2-27 | 2-36 | 2-50 | 3-6 | 4-3 |
| 2-1 | 2-10 | 2-19 | 2-28 | 2-37 | 2-52 | 3-8 | 4-4 |
| 2-2 | 2-11 | 2-20 | 2-29 | 2-38 | 2-58 | 3-9 | 4-5 |
| 2-3 | 2-12 | 2-21 | 2-30 | 2-39 | 2-63 | 3-10 | |
| 2-4 | 2-13 | 2-22 | 2-31 | 2-44 | 2-64 | 3-11 | |
| 2-5 | 2-14 | 2-23 | 2-32 | 2-45 | 3-1 | 3-12 | |
| 2-6 | 2-15 | 2-24 | 2-33 | 2-46 | 3-2 | 3-13 | |
| 2-7 | 2-16 | 2-25 | 2-34 | 2-48 | 3-4 | 4-1 | |

(Test Example 2) Efficacy Test 1 Against *Tetranychus urticae*

Kidney bean plants were raised in No. 3 pots, and 8 adult females of organophosphorus-resistant *Tetranychus urticae* were inoculated on primary leaves. Then, the emulsion (I) was diluted with water so that the concentration of the compound was 125 ppm to obtain a chemical. This chemical was sprayed on the kidney bean plants. The kidney bean plants were placed in a thermostatic chamber at a temperature of 25° C. and a humidity of 65%. The life and death of *Tetranychus urticae* were investigated when 10 days had passed after the chemical spraying.

The compounds with compound numbers 1-1, 1-2, 2-1 and 2-2 were tested for efficacy against *Tetranychus urticae*. All compounds showed an insecticidal rate of 90% or more against *Tetranychus urticae*.

(Test Example 3) Efficacy Test 1 Against *Panonychus citri*

8 adult females of *Panonychus citri* from Kanagawa Prefecture were inoculated on mandarin orange leaves placed in a petri dish. Then, the emulsion (I) was diluted with water so that the concentration of the compound was 125 ppm to obtain a chemical. This chemical was sprayed onto the mandarin orange leaves with a rotary spray tower. The mandarin orange leaves were placed in a thermostatic chamber at a temperature of 25° C. and a humidity of 65%. The life and death of *Panonychus citri* were investigated when 10 days had passed after the chemical spraying.

The compounds with compound numbers 1-1, 1-2, 2-1 and 2-2 were tested for efficacy against *Panonychus citri*. All compounds showed an insecticidal rate of 90% or more against *Panonychus citri*.

(Test Example 4) Efficacy Test Against *Aculops pelekassi*

20 adult females of *Aculops pelekassi* from Ehime Prefecture were inoculated on mandarin orange leaves placed in a petri dish. Then, the emulsion (I) was diluted with water so that the concentration of the compound was 125 ppm to obtain a chemical. This chemical was sprayed onto the mandarin orange leaves with a rotary spray tower. The mandarin orange leaves were placed in a thermostatic chamber at a temperature of 25° C. and a humidity of 65%. The life and death of *Aculops pelekassi* were investigated when 10 days had passed after the chemical spraying.

The compounds with compound numbers 1-1 and 1-2 were tested for efficacy against *Aculops pelekassi*. All compounds showed an insecticidal rate of 90% or more against *Aculops pelekassi*.

(Test Example 5) Efficacy Test 2 Against *Tetranychus urticae*

8 adult females of *Tetranychus urticae* from Shizuoka Prefecture were inoculated on kidney bean plant leaves placed in a petri dish. Then, the emulsion (I) was diluted with water so that the concentration of the compound was 125 ppm to obtain a chemical. This chemical was sprayed onto the kidney bean plant leaves with a rotary spray tower. The kidney bean plant leaves were placed in a thermostatic chamber at a temperature of 25° C. and a humidity of 65%. The life and death of *Tetranychus urticae* were investigated when 10 days had passed after the chemical spraying.

The compounds with numbers shown in Table 7 were tested for efficacy against *Tetranychus urticae*. All compounds showed an insecticidal rate of 90% or more against *Tetranychus urticae*.

TABLE 7

| 1-1 | 2-5 | 2-20 | 2-30 |
| 1-2 | 2-6 | 2-21 | 2-31 |
| 2-1 | 2-7 | 2-27 | 2-48 |
| 2-2 | 2-8 | 2-28 | |
| 2-3 | 2-9 | 2-29 | |

(Test Example 6) Efficacy Test 3 Against
*Tetranychus urticae*

8 adult females of *Tetranychus urticae* from Aomori Prefecture were inoculated on kidney bean plant leaves placed in a petri dish. Then, the emulsion (I) was diluted with water so that the concentration of the compound was 125 ppm to obtain a chemical. This chemical was sprayed onto the kidney bean plant leaves with a rotary spray tower. The kidney bean plant leaves were placed in a thermostatic chamber at a temperature of 25° C. and a humidity of 65%. The life and death of *Tetranychus urticae* were investigated when 10 days had passed after the chemical spraying.

The compounds with numbers shown in Table 8 were tested for efficacy against *Tetranychus urticae*. All compounds showed an insecticidal rate of 90% or more against *Tetranychus urticae*.

TABLE 8

| 1-1 | 2-3 | 2-9 | 2-64 | 4-5 |
|---|---|---|---|---|
| 1-2 | 2-5 | 2-26 | 4-1 | |
| 2-1 | 2-6 | 2-31 | 4-2 | |
| 2-2 | 2-7 | 2-48 | 4-3 | |

(Test Example 7) Efficacy Test 2 Against
*Panonychus citri*

8 adult females of *Panonychus citri* from Aichi Prefecture were inoculated on mandarin orange leaves placed in a petri dish. Then, the emulsion (I) was diluted with water so that the concentration of the compound was 125 ppm to obtain a chemical. This chemical was sprayed onto the mandarin orange leaves with a rotary spray tower. The mandarin orange leaves were placed in a thermostatic chamber at a temperature of 25° C. and a humidity of 65%. The life and death of *Panonychus citri* were investigated when 10 days had passed after the chemical spraying.

The compounds with numbers shown in Table 9 were tested for efficacy against *Panonychus citri*. All compounds showed an insecticidal rate of 90% or more against *Panonychus citri*.

TABLE 9

| 1-1 | 2-6 | 2-28 | 2-63 | 4-5 |
|---|---|---|---|---|
| 1-2 | 2-7 | 2-29 | 2-64 | |
| 2-1 | 2-8 | 2-31 | 4-1 | |
| 2-2 | 2-9 | 2-33 | 4-2 | |
| 2-5 | 2-26 | 2-34 | 4-3 | |

(Test Example 8) Efficacy Test 3 Against
*Panonychus citri*

8 adult females of *Panonychus citri* from Wakayama Prefecture were inoculated on mandarin orange leaves placed in a petri dish. Then, the emulsion (I) was diluted with water so that the concentration of the compound was 125 ppm to obtain a chemical. This chemical was sprayed onto the mandarin orange leaves with a rotary spray tower. The mandarin orange leaves were placed in a thermostatic chamber at a temperature of 25° C. and a humidity of 65%. The life and death of *Panonychus citri* were investigated when 10 days had passed after the chemical spraying.

The compounds with numbers shown in Table 10 were tested for efficacy against *Panonychus citri*. All compounds showed an insecticidal rate of 90% or more against *Panonychus citri*.

TABLE 10

| 1-1 | 2-5 | 2-28 | 2-34 |
|---|---|---|---|
| 1-2 | 2-6 | 2-29 | 2-63 |
| 2-1 | 2-7 | 2-30 | 2-64 |
| 2-2 | 2-8 | 2-31 | |
| 2-3 | 2-9 | 2-32 | |
| 2-4 | 2-26 | 2-33 | |

(Test Example 9) Efficacy Test Against *Tetranychus urticae* (Root Dipping Test)

The emulsion (I) was diluted with tap water to prepare a drug solution having a concentration of 9.4 ppm. The root portions of kidney bean seedlings (primary leaf stage) were washed to expose the roots and dipped in the drug solution for treatment. Thereafter, they were placed in a thermostatic chamber at a temperature of 25° C. and a humidity of 60%. Three days after the dipping treatment, 10 adult females of *Tetranychus urticae* were inoculated on each seedling. The number of surviving adult females 14 days after inoculation was investigated, and the control value was obtained by the following formula. The test was repeated twice.

Control value (%)=100−{(Nt)/(Nc)×100}

The letters in the formula represent the following.
Nc: Number of surviving insects in the untreated group
Nt: Number of surviving insects in the treated group The compounds with compound numbers 1-1, 1-2, 2-1 and 2-2 were tested for efficacy against *Tetranychus urticae*. All compounds showed a control value of 90% or more against *Tetranychus urticae*.

(Test Example 10) Efficacy Test Against
*Tetranychus urticae* (Soil Irrigation Test)

The emulsion (I) was diluted with tap water to prepare a drug solution having a concentration of 400 ppm. A plastic potted strawberry seedling was subjected to a plant foot irrigation treatment with 25 ml of the drug solution, and placed in a thermostatic chamber at a temperature of 25° C. and a humidity of 60%. Three days after the irrigation treatment, 15 adult females of *Tetranychus urticae* were inoculated on each seedling. The number of surviving insects 19 days after inoculation was investigated, and the control value was obtained by the following formula. The test was repeated twice.

Control value (%)=100−{(Nt)/(Nc)×100}

The letters in the formula represent the following.
Nc: Number of surviving insects in the untreated group
Nt: Number of surviving insects in the treated group The compound with a compound number 1-1 was tested for efficacy against *Tetranychus urticae*. As a result, it showed a control value of 90% or more against *Tetranychus urticae*.

(Test Example 11) Efficacy Test Against *Ascaridia galli* and *Oesophagostomum dentatum*

The biological activity of the compounds according to the present invention was investigated in vitro using two kinds of parasites in gut-welling larval stages: *Ascaridia galli* at the third larval stage ("L3"); and *Oesophagostomum dentatum* at the third and fourth larval stages ("L3" and "L4" respectively). When performing these tests, DMSO solutions containing the compound according to the present invention at various concentrations were prepared and incubated in 96-well microtiter plates. Then, parasites were inoculated at 20 larvae per well. The biological activity was investigated by microscopic examination. The microscopic examination includes evaluation of mortality, damage, motility, progression of development, and neutral red uptake by the larval parasites in comparison with those of DMSO control. The biological activity was defined by the minimum effective concentration ("MEC"), which is a concentration where at least one of the larval parasites shows changes in mortality, damage or motility, changes in progression of development, or no neutral red uptake.

The compounds with compound numbers 1-1, 1-2, 2-1, 2-2, 2-3, 2-4, 2-5, 2-6, 2-7, 2-8, 2-9 and 2-10 were tested for efficacy against *Ascaridia galli* and *Oesophagostomum dentatum*. All compounds showed activities against one or more target parasites at an MEC of 25 M or less.

(Test Example 12) Efficacy Test Against *Haemonchus contortus*

The biological activity of the compounds according to the present invention was investigated in vitro by preparing *Haemonchus contortus* at the third larval stage ("L3") from feces of infected sheep. When performing these tests, DMSO solutions containing the compound according to the present invention at various concentrations were prepared and incubated in 96-well microtiter plates. Then, parasites were inoculated at 100 larvae per well. The biological activity was investigated by microscopic examination. The microscopic examination includes evaluation of mortality, damage, motility, progression of development, and neutral red uptake by the larval parasites in comparison with those of DMSO control. The biological activity was defined by the minimum effective concentration ("MEC"), which is a concentration where at least one of the larval parasites shows changes in mortality, damage or motility, changes in progression of development, or no neutral red uptake.

The compounds with compound numbers 1-1 and 2-3 were tested for efficacy against *Haemonchus contortus*. All compounds showed activity against L3 *Haemonchus contortus* at an MEC of 25 M or less.

Then, it is shown that the compound (II) (compound No. 1-1) of the present invention is particularly useful as an active ingredient of an acaricide by tests against acaricide resistant strains of spider mites and phytotoxicity tests. The compounds used for comparison and control are compounds (D), (G) and (H) shown below.

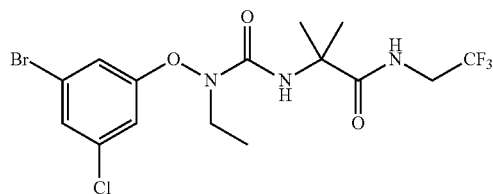 [SMILES: CCN(Oc1cc(Cl)cc(Br)c1)C(=O)NC(C)(C)C(=O)NCC(F)(F)F]

(D) (described in Patent Document 2)

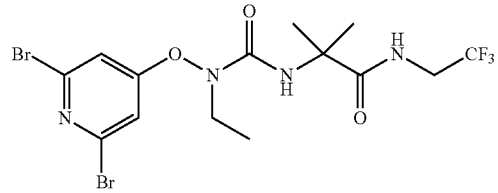 [SMILES: CCN(Oc1cc(Br)nc(Br)c1)C(=O)NC(C)(C)C(=O)NCC(F)(F)F]

(G) (described in Patent Document 5)

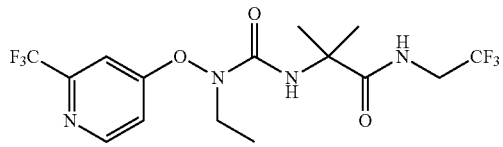 [SMILES: CCN(Oc1ccnc(C(F)(F)F)c1)C(=O)NC(C)(C)C(=O)NCC(F)(F)F]

(H) (described in Patent Document 5)

(Test Example 13) Efficacy Test Against Drug-Resistant Strains of Spider Mites

Efficacy tests against seven drug-resistant strains of *Tetranychus urticae* collected from various parts of Japan (one strain from Shizuoka Prefecture, Aomori Prefecture and Fukuoka Prefecture, and two strains from Chiba Prefecture and Nagano Prefecture) were conducted in the following manner.

8 adult females of drug-resistant strains of spider mites were inoculated on kidney bean plant leaves placed in a petri dish. Then, the emulsion (I) was diluted with water so that the concentration of the compound was 37.5 ppm or 9.4 ppm to obtain a chemical. This chemical was sprayed onto the kidney bean plant leaves with a rotary spray tower. The kidney bean plant leaves were placed in a thermostatic chamber at a temperature of 25° C. and a humidity of 65%. The life and death of the spider mite were investigated when 10 days had passed after the spraying, and the insecticidal rate was calculated.

In addition, an efficacy test against a drug-resistant strain of *Panonychus citri* collected in Wakayama Prefecture was conducted in the following manner.

8 adult females of a drug resistant strain of *Panonychus citri* were inoculated on mandarin orange leaves placed in a petri dish. Then, the emulsion (I) was diluted with water so that the concentration of the compound was 37.5 ppm or 9.4 ppm to obtain a chemical. This chemical was sprayed onto the mandarin orange leaves with a rotary spray tower. The mandarin orange leaves were placed in a thermostatic chamber at a temperature of 25° C. and a humidity of 65%. The life and death of the spider mite were investigated when 10 days had passed after the spraying, and the corrected insecticidal rate was calculated.

The test results of the drug resistant strains of spider mites are shown in Table 11.

TABLE 11

| Test compound | Concentration (ppm) | Low-susceptible Tetranychus urticae from Shizuoka Prefecture | Low-susceptible Tetranychus urticae from Aomori Prefecture | Low-susceptible Tetranychus urticae from Fukuoka Prefecture | Low-susceptible Tetranychus urticae 1 from Chiba Prefecture |
|---|---|---|---|---|---|
| 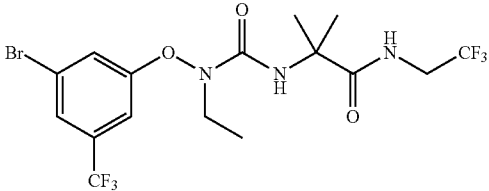 Compound (II) | 37.5<br>9.4 | 100<br>96 | 100<br>93 | 99<br>96 | 100<br>100 |
| 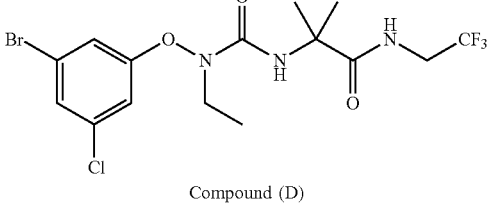 Compound (D) | 37.5<br>9.4 | —<br>— | —<br>— | —<br>— | 77<br>32 |
| 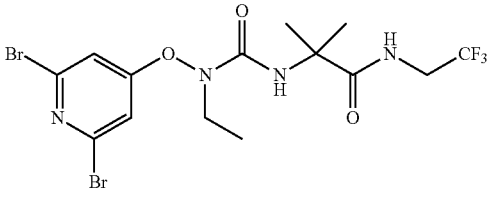 Compound (G) | 37.5<br>9.4 | —<br>— | 97<br>66 | —<br>— | 98<br>53 |
| 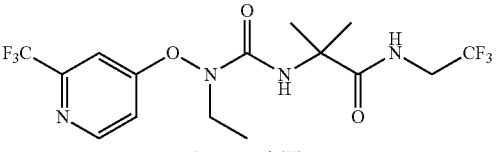 Compound (H) | 37.5<br>9.4 | —<br>— | —<br>— | 96<br>45 | —<br>— |

| | Low-susceptible Tetranychus urticae 2 from Chiba Prefecture | Low-susceptible Tetranychus urticae 1 from Nagano Prefecture | Low-susceptible Tetranychus urticae 2 from Nagano Prefecture | Low-susceptible Panonychus citri from Wakayama Prefecture |
|---|---|---|---|---|
| 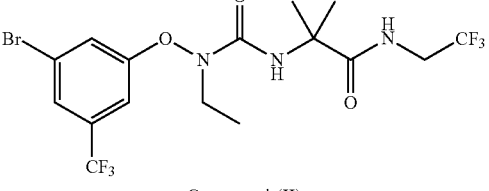 Compound (II) | 100<br>97 | 100<br>100 | 100<br>99 | 100<br>99 |
| 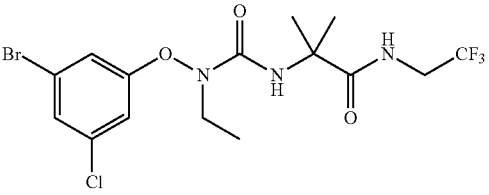 [SMILES: CCN(Oc1cc(Cl)cc(Br)c1)C(=O)NC(C)(C)C(=O)NCC(F)(F)F] Compound (D) | 87<br>72 | 99<br>73 | 96<br>45 | —<br>— |

TABLE 11-continued

| Structure | | | | |
|---|---|---|---|---|
| 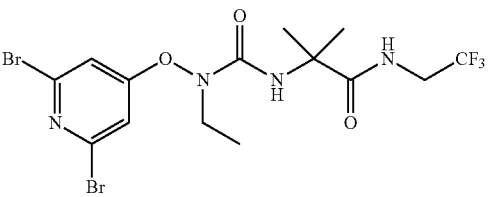 [SMILES: CCN(Oc1cc(Br)nc(Br)c1)C(=O)NC(C)(C)C(=O)NCC(F)(F)F]<br>Compound (G) | 91<br>58 | 96<br>78 | 88<br>70 | 95<br>60 |
| 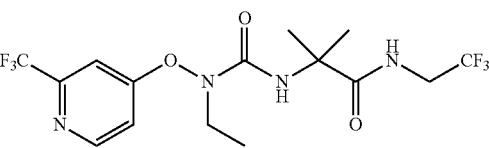 [SMILES: CCN(Oc1ccnc(C(F)(F)F)c1)C(=O)NC(C)(C)C(=O)NCC(F)(F)F]<br>Compound (H) | —<br>— | —<br>— | —<br>— | 96<br>78 |

\* Numerical values in the table indicate insecticidal rates

As shown in the test example, the compound (II) (compound No. 1-1) of the present invention showed an efficacy of 90 or more against all drug resistant strains of spider mites at a compound concentration of 9.4 ppm. On the other hand, the compounds (D), (G) and (H) showed an efficacy of less than 90 against some resistant strains of spider mites at a concentration of 9.4 ppm. From these results, it is clear that the compound (II) (compound No. 1-1) of the present invention is superior to the compounds (D), (G) and (H).

(Test Example 14) Phytotoxicity and Efficacy Tests

A test for phytotoxicity on cucumber plants was conducted as follows. A sufficient amount of chemical having a compound concentration of 300 ppm was sprayed onto cucumber plants at the 1.5-leaf stage using a glass nozzle, and they were left to stand in a greenhouse. The presence or absence of phytotoxicity was investigated after being left to stand for 14 days. The phytotoxicity was indexed into 11 levels with scores from 0 (no phytotoxicity) to 10 (plant death).

In addition, a test for phytotoxicity on eggplants was conducted as follows.

A sufficient amount of chemical having a compound concentration of 300 ppm was sprayed onto eggplants at the 6- to 7-leaf stage using a glass nozzle, and they were left to stand in a greenhouse. The presence or absence of phytotoxicity was investigated after being left to stand for 14 days. The phytotoxicity was indexed into 11 levels with scores from 0 (no phytotoxicity) to 10 (plant death).

The results of the phytotoxicity tests are shown in Table 12. The symptoms of phytotoxicity were deformation and discoloration of leaves.

TABLE 12

| Test Compound | Concentration (ppm) | Repetition | Cucumber; 1.5-leaf stage After 14 days Leaf Phytotoxicity index | Eggplant; 6- to 7-leaf stage After 14 days Leaf Phytotoxicity index |
|---|---|---|---|---|
| 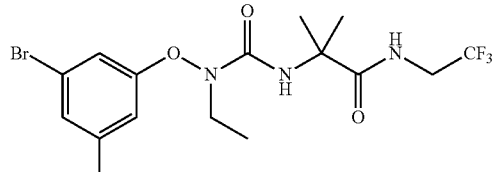<br>Compound (II) | 300 | A<br>B | 0<br>0 | 0<br>0 |
| 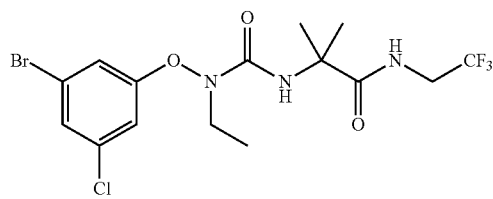 [SMILES: CCN(Oc1cc(Cl)cc(Br)c1)C(=O)NC(C)(C)C(=O)NCC(F)(F)F]<br>Compound (D) | 300 | A<br>B | 5<br>7 | 3<br>3 |

TABLE 12-continued

| Test Compound | Concentration (ppm) | Repetition | Cucumber; 1.5-leaf stage After 14 days Leaf Phytotoxicity index | Eggplant; 6- to 7-leaf stage After 14 days Leaf Phytotoxicity index |
|---|---|---|---|---|
| Compound (G) | 300 | A | 2 | 2 |
|  |  | B | 2 | 2 |
| Compound (H) | 300 | A | — | 2 |
|  |  | B | — | 2 |

As shown in the test example, the compound (II) (compound No. 1-1) of the present invention causes no phytotoxicity on cucumber plants and eggplants. From these results, it is clear that the compound (II) (compound No. 1-1) of the present invention is superior to the compounds (D), (G) and (H).

Since those randomly selected from among the compounds of the present invention exert the above-mentioned effects, it can be understood that the compounds of the present invention including the compounds that are not exemplified are compounds having the effects of pest control, in particular, insecticidal, acaricidal and ectoparasiticidal effects and the like, which causes no phytotoxicity to plant bodies, with little toxicity to humans, animals and fish and little impact on the environment.

INDUSTRIAL APPLICABILITY

It is possible to provide a phenoxyurea compound which is excellent in pest control activity such as insecticidal/acaricidal activities and nematicidal activity, excellent in safety and can be synthesized in an industrially favorable manner; and a pest control agent containing this compound as an active ingredient.

The invention claimed is:
1. A compound of formula (II) or a salt thereof

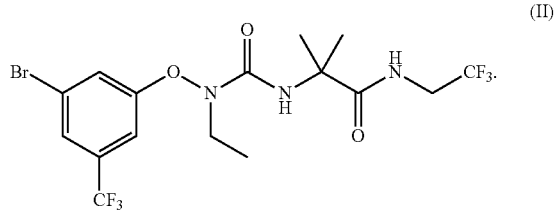 [SMILES: CCN(Oc1cc(Br)cc(C(F)(F)F)c1)C(=O)NC(C)(C)C(=O)NCC(F)(F)F]

(II)

2. An acaricidal agent comprising the compounds according to claim 1 and/or a salt thereof as an active ingredient.

* * * * *

UNITED STATES PATENT AND TRADEMARK OFFICE
CERTIFICATE OF CORRECTION

PATENT NO. : 11,044,911 B2
APPLICATION NO. : 17/045418
DATED : June 29, 2021
INVENTOR(S) : Furukawa et al.

Page 1 of 1

It is certified that error appears in the above-identified patent and that said Letters Patent is hereby corrected as shown below:

In the Claims

Column 54, Claim 1, Line 40, should be

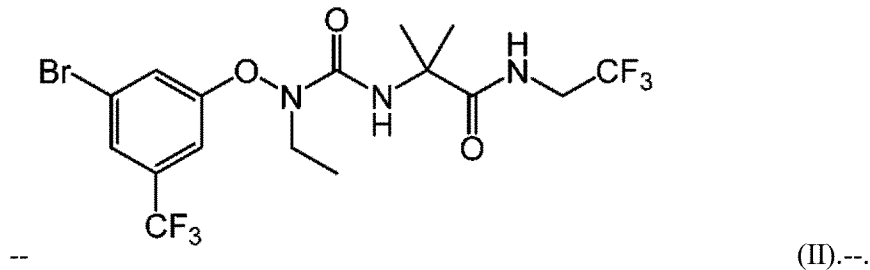

-- (II).--.

Column 54, Claim 2, Line 45, "compounds" should be --compound--.

Signed and Sealed this
Thirtieth Day of November, 2021

Drew Hirshfeld
*Performing the Functions and Duties of the
Under Secretary of Commerce for Intellectual Property and
Director of the United States Patent and Trademark Office*